(12) United States Patent
Sudhakar et al.

(10) Patent No.: US 8,802,719 B2
(45) Date of Patent: Aug. 12, 2014

(54) METHOD OF PREPARING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID

(71) Applicant: Sunesis Pharmaceuticals, Inc., South San Francisco, CA (US)

(72) Inventors: Anantha Sudhakar, Fremont, CA (US); Tamilarasan Subramani, Karur (IN); Mohamed Shiek Mohamed Mujeebur Rahuman, Bangalore (IN); Ramar Subbiah, Hosur (IN)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/940,157

(22) Filed: Jul. 11, 2013

(65) Prior Publication Data

US 2014/0171660 A1   Jun. 19, 2014

Related U.S. Application Data

(63) Continuation of application No. 12/650,390, filed on Dec. 30, 2009, now Pat. No. 8,497,282.

(60) Provisional application No. 61/141,856, filed on Dec. 31, 2008.

(51) Int. Cl.
*A61K 31/4015* (2006.01)
*C07D 207/12* (2006.01)
*C07D 207/14* (2006.01)

(52) U.S. Cl.
USPC ..................... 514/424; 548/541; 514/426

(58) Field of Classification Search
CPC . A61K 31/4015; C07D 207/12; C07D 207/14
USPC ................... 514/424, 426; 548/541
See application file for complete search history.

(56) References Cited

U.S. PATENT DOCUMENTS

| 5,134,127 | A | 7/1992 | Stella et al. |
|---|---|---|---|
| 5,817,669 | A | 10/1998 | Tomita et al. |
| 7,968,565 | B2 | 6/2011 | Arkin et al. |
| 7,989,468 | B2 | 8/2011 | Adelman et al. |
| 8,124,773 | B2 | 2/2012 | Adelman et al. |
| 8,138,202 | B2 | 3/2012 | Sudhakar et al. |
| 2006/0025437 | A1 | 2/2006 | Adelman et al. |
| 2008/0063642 | A1 | 3/2008 | Adelman et al. |
| 2009/0263393 | A1 | 10/2009 | Adelman et al. |
| 2010/0029708 | A1 | 2/2010 | Adelman et al. |
| 2010/0048609 | A1 | 2/2010 | Jacobs |
| 2010/0297142 | A1 | 11/2010 | Silverman |
| 2011/0008371 | A1 | 1/2011 | Michelson |
| 2011/0082169 | A1 | 4/2011 | Sudhakar et al. |
| 2011/0105497 | A1 | 5/2011 | Sudhakar |

FOREIGN PATENT DOCUMENTS

| JP | 62033176 | 2/1987 |
|---|---|---|
| JP | 9221424 | 8/1997 |
| JP | 11-349565 | 6/1998 |
| JP | 2003/127542 | 5/2003 |
| WO | WO 2010/099526 | 2/2010 |

OTHER PUBLICATIONS

Tsuzuki et al., Tet. Asym., 2001,1793-1799, vol. 12.*
Kumar et al., Tet. Lett., 2003, 5687-5689, vol. 44.
Tsuzuki, et al., J. Med. Chem., 2004, 2097-2106, vol. 47.
Tomita, et al., J. Med. Chem., 2002, 5564-5575, vol. 45.
Tsuzuki et al., Tet. Asym., 2001, 2989-2997, vol. 12.
Office Action dated Dec. 13, 2012 issued in U.S. Appl. No. 12/650,390.
Notice of Allowance dated Mar. 28, 2013 issued in U.S. Appl. No. 12/650,390.

* cited by examiner

*Primary Examiner* — Kamal Saeed
*Assistant Examiner* — Janet L Coppins
(74) *Attorney, Agent, or Firm* — Jones Day

(57) ABSTRACT

Methods of preparing (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid are disclosed. Also provided are pharmaceutical compositions comprising (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and methods of treatment using such compositions.

1 Claim, No Drawings

METHOD OF PREPARING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID

1. RELATED APPLICATIONS

This application claims priority under 35 U.S.C. §120 to, and is a continuation of, U.S. application Ser. No. 12/650,390, filed Dec. 30, 2009, which claims priority to U.S. Provisional Application Ser. No. 61/141,856 filed Dec. 31, 2008. The disclosure of each of the above referenced applications is incorporated by reference herein in its entirety.

2. FIELD

Provided herein are methods for preparing (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, methods for preparing intermediates useful in the preparation of the compound, compositions comprising the compound, methods of use of such compositions for treatment of cancer and methods of using the intermediates in preparing (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

3. BACKGROUND

The compound (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, having the structure:

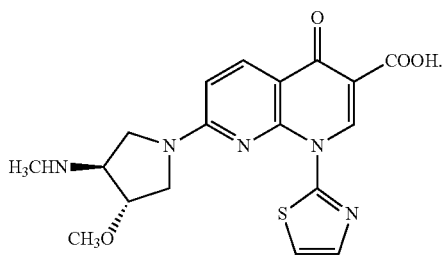

is also known as SNS-595 or AG-7352. The United States Adopted Names Council (USANC) has assigned the name "Voreloxin" to this compound.

SNS-595 is known for its anti-tumor activity (see, Tsuzuki et al., *J. Med. Chem.*, 47:2097-2106, 2004 and Tomita et al., *J. Med. Chem.*, 45:5564-5575, 2002). Treatment of various cancers with SNS-595 has been proposed in the literature, and has shown preclinical activity against various cancer cell lines and xenografts. Various dosing regimens for the use of this compound have been reported. For example, see U.S. Patent Application Pub. Nos. 2005-0203120 A1; 2005-0215583 A1 and 2006-0025437 A1, all of which are incorporated herein by reference in their entireties. SNS-595 is presently being tested in clinical trials to assess safety and efficacy in human cancer patients, and has demonstrated clinical activity against acute myeloid leukemia and ovarian cancer.

SNS-595 can be prepared using techniques known to one of skill in the art. See, for example, U.S. Pat. No. 5,817,669, issued Oct. 6, 1998, Japanese Patent Application No. Hei 10-173986, published Jun. 26, 1998, WO 2007/146335, Tsuzuki et al., *J. Med. Chem.*, 47:2097-2106, 2004 and Tomita et al., *J. Med. Chem.*, 45: 5564-5575, 2002, which are incorporated herein by reference in their entirety.

Conventional methods of preparing SNS-595 can yield compositions comprising other compounds that either result from side reactions that occur during the SNS-595 synthesis process or are reagents that remain unreacted.

International patent application WO 2007/146335, published Dec. 21, 2007, describes preparation of a composition that comprises SNS-595 and (+)-1,4-dihydro-7-[(3S,4S)-3-methoxy-4-amino-1-pyrrolidinyl]-4-oxo-1-(2-thiazolyl)-1,8-naphthyridine-3-carboxylic acid, which is described therein as an "N-desmethyl" compound. Data are presented indicating that the N-desmethyl compound is shown to be active in a cytotoxicity assay. The N-desmethyl compound is a significant side product of the conventional approach to synthesizing SNS-595.

Thus, there remains a need for improved methods for preparing SNS-595 substantially free of contaminants, to provide the compound in a substantially pure form well suited for formulation into pharmaceutical compositions for the treatment of cancer without the need for laborious purification steps.

4. SUMMARY

Although certain by-products are known to exist in SNS-595 preparation, reducing the amount of such in the final drug product is important. Since cancer patients undergo significant chemotherapy and radiation and can often have compromised immune systems, it is beneficial to deliver highly pure drug to cancer patients. Further, for parenteral administration, the purity and percentage of the drug delivered is extremely important because the drug enters directly into the blood stream. As a result, described herein are processes that can yield substantially pure SNS-595. In addition, the processes provided can be scaled up to commercial manufacturing of substantially pure SNS-595.

In one embodiment, provided herein is a process for preparing intermediates required in the preparation of SNS-595.

In certain embodiments, provided herein are processes for preparation of SNS-595. In certain embodiments, the processes provided herein yield compositions comprising SNS-595 and N-desmethyl-SNS-595. In one embodiment, provided herein is a process for preparing intermediates useful in the preparation of SNS-595.

In one embodiment, provided herein is a process for preparing SNS-595 as illustrated in Schemes 1 and 2.

Scheme 1

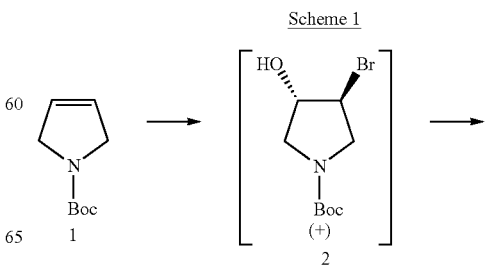

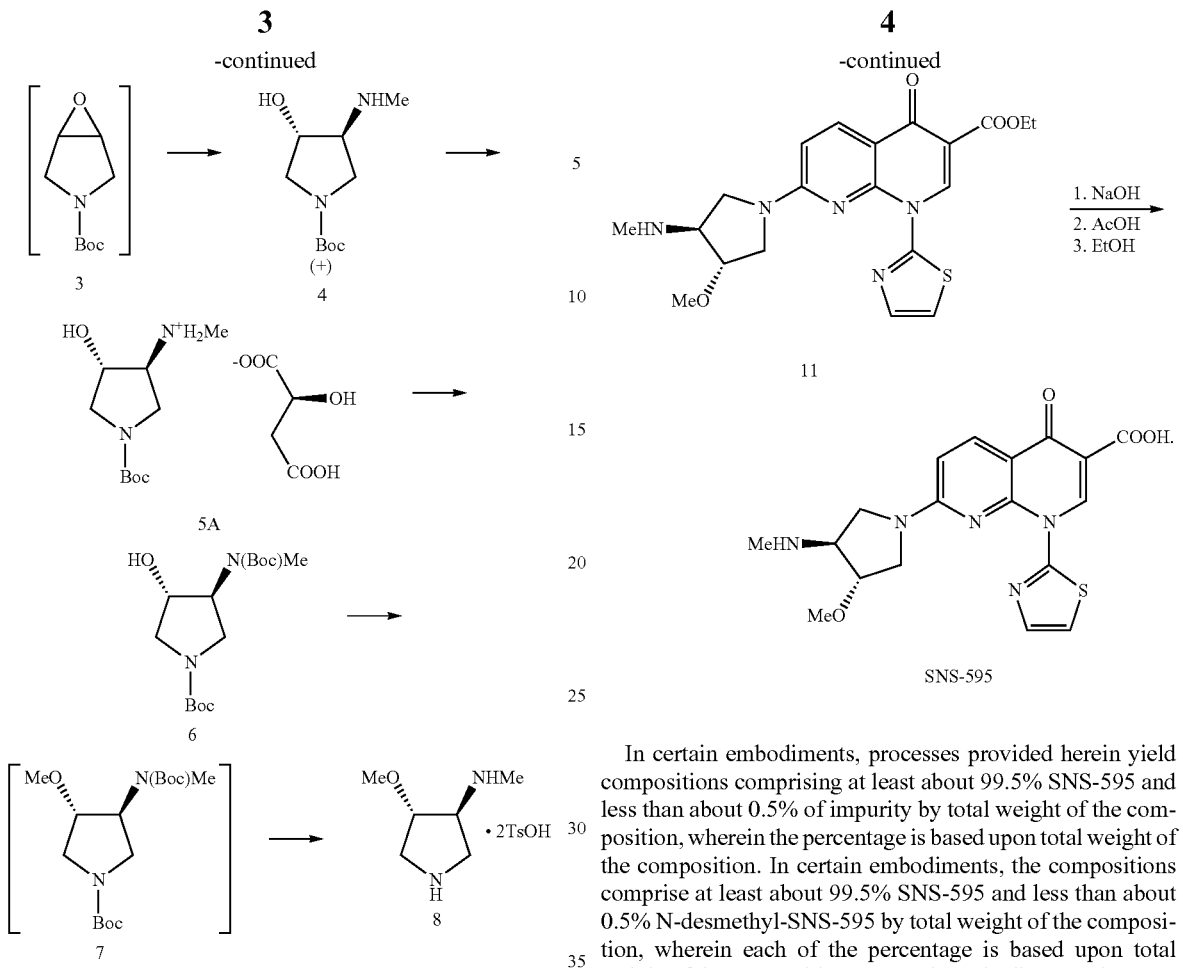

In this route, Compound 4 is obtained by nucleophilic opening of epoxide (Compound 3) by methylamine, thereby eliminating the impurities resulting from incomplete methylation. In certain embodiments, Compound 2 is directly converted to Compound 4 by treatment with methylamine and a base, such as sodium bicarbonate. Compound 4 is resolved by reaction with a chiral acid, such as L-(−)-malic acid or L-(−)-pyroglutamic acid to form a chiral salt.

Compound 8, prepared according to Scheme 1 or otherwise, is then reacted with 7-chloro-4-oxo-1-thiazol-2-yl-1,4-dihydro-[1,8]naphthyridine-3-carboxylic acid ethyl ester to obtain SNS-595 as illustrated in Scheme 2.

Scheme 2

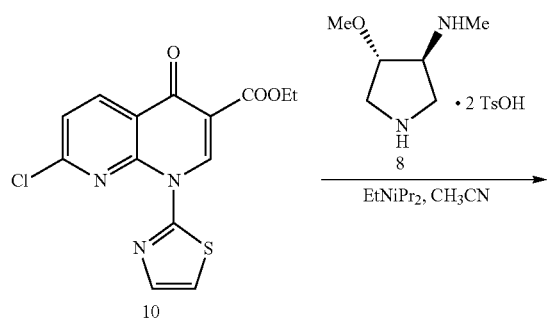

In certain embodiments, processes provided herein yield compositions comprising at least about 99.5% SNS-595 and less than about 0.5% of impurity by total weight of the composition, wherein the percentage is based upon total weight of the composition. In certain embodiments, the compositions comprise at least about 99.5% SNS-595 and less than about 0.5% N-desmethyl-SNS-595 by total weight of the composition, wherein each of the percentage is based upon total weight of the composition. In certain embodiments, the compositions comprise at least about 99.5% SNS-595 and less than about 0.5% O-desmethyl-SNS-595 by total weight of the composition, wherein each of the percentage is based upon total weight of the composition. In certain embodiments, the compositions comprise at least about 99.5% SNS-595 and less than about 0.5% total O-desmethyl-SNS-595 and N-desmethyl-SNS-595 by total weight of the composition, wherein each of the percentage is based upon total weight of the composition. In certain embodiments, the compositions comprise at least about 99.5% SNS-595 and less than about 0.5% N,O-bisdesmethyl-SNS-595 by total weight of the composition, wherein each of the percentage is based upon total weight of the composition. In certain embodiments, the compositions comprise at least about 99.5% SNS-595 and less than about 0.5% total O-desmethyl-SNS-595, N-desmethyl-SNS-595 and N,O-bisdesmethyl-SNS-595 by total weight of the composition, wherein each of the percentage is based upon total weight of the composition.

In certain embodiments, provided herein is a scale-up process for preparing substantially pure SNS-595.

In certain embodiments, the compositions are useful in the methods of treating, preventing or managing one or more cancers in a human or other subject.

In certain embodiments, provided herein are pharmaceutical compositions comprising substantially pure SNS-595 for treatment of cancer. The types of cancers that can be treated, prevented, or managed using methods provided herein include, but are not limited to solid tumors and blood-borne tumors.

Also provided are methods of preparing the compositions and compounds described herein. In certain embodiments provided herein are intermediates useful in preparing SNS-595.

5. DETAILED DESCRIPTION

5.1 Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "protecting group" is any of the well recognized protecting groups for active groups in a molecule. In processes described herein the free groups include, hydroxyl, amino and carboxy. Exemplary protecting groups include, but are not limited to, benzyloxycarbonyl, t-butoxycarbonyl, and the like. As used herein, "protection reaction" refers to a reaction in which an active group is blocked with a protecting group to avoid undesired reactions with the active group. As used herein, "protecting" refers to blocking an active group on a compound with protecting group to avoid undesired reactions with the active group. As used herein, "deprotection reaction" refers to a reaction in which the protecting group is removed to regenerate the active group. As used herein, "deprotecting" refers removing a protecting group on a compound to regenerate the active group. For example, t-butoxycarbonyl protecting group can be removed from an amino group by reaction with deprotecting reagents such as HCl/MeOH, trimethylsilane or p-toluene sulfonic acid monohydrate.

As used herein, "epoxide opening" refers to a reaction in which an epoxide ring is opened with a nucleophile, such as a primary amine, for example methylamine, to yield a compound containing a free hydroxyl group.

As used herein, "methylation" refers to a reaction in which a free hydroxyl or amine group undergoes a reaction with a methylating agent wherein a hydrogen is replaced by a methyl group. The methylation reaction can be accomplished with, for example, dimethyl sulfate.

As used herein, "methylating" refers to replacing a hydrogen in a hydroxyl or an amine group by a methyl group through a reaction with a methylating agent. The methylation reaction can be accomplished with, for example, dimethyl sulfate.

As used herein "resolution" or "chiral resolution" refers to a process for the separation of racemic compounds into their enantiomers.

As used herein "resolving" refers to separating a racemic compound into its enantiomers.

As used herein "commercial scale" or "process scale" refers to a process for SNS-595 that yields greater than 1 kilogram of SNS-595.

As used herein, "impurity" refers to chemical species other than (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid.

As used herein, "SNS-595" means (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid, as well as any ionic form, salts, solvates, e.g., hydrate, or other forms of that compound, including mixtures thereof. Thus, compositions comprising SNS-595 may include (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid or an ionic form thereof, salt, solvate, e.g., hydrate, or other form of the compound. In some embodiments, SNS-595 is provided as a pharmaceutically acceptable salt.

As used herein, "SNS-595 Substance" means a composition consisting essentially of (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid, including less than 0.5% (by mass) of any other individual compound or impurity based on total weight of the composition. In some embodiments, the chemical process provided herein permits kilogram scale synthesis of SNS-595 Substance that includes less than 0.3%, less than 0.2%, less than 0.1%, or less than 0.05% 1,4-dihydro-7-[(3S,4S)-3-methoxy-4-amino-1-pyrrolidinyl]-4-oxo-1-(2-thiazolyl)-1,8-naphthyridine-3-carboxylic acid, wherein each of the percentage is based upon total weight of the composition. In some embodiments, the chemical process provided herein permits kilogram scale synthesis of SNS-595 Substance that includes less than 0.3%, less than 0.2%, less than 0.1%, or less than 0.05% 1,4-dihydro-7-[(3S,4S)-3-oxy-4-methylamino-1-pyrrolidinyl]-4-oxo-1-(2-thiazolyl)-1,8-naphthyridine-3-carboxylic acid, wherein each of the percentage is based upon total weight of the composition. In some embodiments, the chemical process provided herein permits kilogram scale synthesis of SNS-595 Substance that includes less than 0.3%, less than 0.2%, less than 0.1%, or less than 0.05% 1,4-dihydro-7-[(3S,4S)-3-methoxy-4-amino-1-pyrrolidinyl]-4-oxo-1-(2-thiazolyl)-1,8-naphthyridine-3-carboxylic acid and 1,4-dihydro-7-[(3S,4S)-3-oxy-4-methylamino-1-pyrrolidinyl]-4-oxo-1-(2-thiazolyl)-1,8-naphthyridine-3-carboxylic acid, wherein each of the percentage is based upon total weight of the composition.

As used herein, "SNS-595 Active Ingredient" or "SNS-595 API (Active Pharmaceutical Ingredient)" means a composition comprising (+)-1,4-dihydro-7-[(3S,4S)-3-methoxy-4-methylamino-1-pyrrolidinyl]-4-oxo-1-(2-thiazolyl)-1,8-naphthyridine-3-carboxylic acid and less than 0.1% 1,4-dihydro-7-[(3S,4S)-3-methoxy-4-amino-1-pyrrolidinyl]-4-oxo-1-(2-thiazolyl)-1,8-naphthyridine-3-carboxylic acid and/or 1,4-dihydro-7-[(3S,4S)-3-oxy-4-methylamino-1-pyrrolidinyl]-4-oxo-1-(2-thiazolyl)-1,8-naphthyridine-3-carboxylic acid where the percentage is based on the total weight of the composition.

As used herein, "N-desmethyl-SNS-595" refers to (+)-1,4-dihydro-7-[(3S,4S)-3-methoxy-4-amino-1-pyrrolidinyl]-4-oxo-1-(2-thiazolyl)-1,8-naphthyridine-3-carboxylic acid and has the following chemical structure:

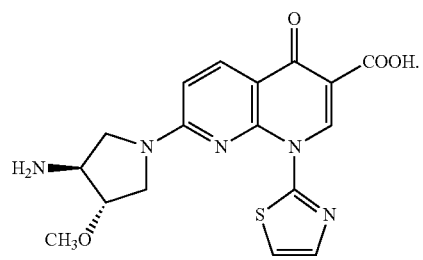

"O-desmethyl-SNS-595" refers to (+)-1,4-dihydro-7-[(3S,4S)-3-hydroxy-4-methylamino-1-pyrrolidinyl]-4-oxo-1-(2-thiazolyl)-1,8-naphthyridine-3-carboxylic acid and has the following chemical structure:

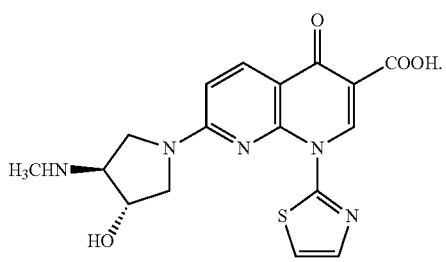

"N,O-bisdesmethyl-SNS-595" refers to (+)-1,4-dihydro-7-[(3S,4S)-3-hydroxy-4-amino-1-pyrrolidinyl]-4-oxo-1-(2-thiazolyl)-1,8-naphthyridine-3-carboxylic acid and has the following chemical structure:

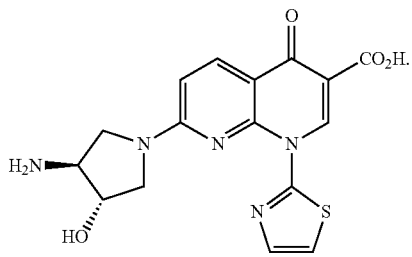 [SMILES: N[C@H]1CN(c2ccc3c(=O)c(C(=O)O)cn(-c4nccs4)c3n2)C[C@@H]1O]

As used herein, "SNS-595 Product" means an aqueous composition of SNS-595 comprising about 10 mg/mL SNS-595 API, about 45 mg/mL D-sorbitol, and an organic acid, prepared in water, in which the pH of the composition is about 2.3-2.7. In some embodiments, the organic acid is methanesulfonic acid. In some embodiments, the pH of the SNS-595 Product is about 2.5. In some embodiments, the SNS-595 Product is sterile.

As used herein, "composition" refers to a composition of SNS-595 and impurities having a thiazolyl-oxo-naphthyridine-3-carboxylic acid scaffold. Such impurities include N-desmethyl-SNS-595, O-desmethyl-SNS-595 and N,O-bisdesmethyl-SNS-595.

As used herein, the term "substantially pure" with respect to SNS-595 refers to a composition that includes at least about 99.5%, 99.6%, 99.7%, 99.8%, 99.9% or up to about 100% by weight of SNS-595, the remainder comprising other chemical species. The purity of SNS-595 provided herein can be determined by standard methods of analysis, such as high performance liquid chromatography (HPLC), used by those of skill in the art to assess such purity. In certain embodiments, SNS-595 is sufficiently pure such that further purification would not detectably alter the physical and chemical properties, such as biological activity, of the compound.

As used herein, "enantiomerically pure SNS-595" refers to SNS-595 that is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (i.e., in enantiomeric excess). In other words, SNS-595 is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and is, thus, in enantiomeric excess of the "(−)" form. The term "enantiomerically pure" or "pure enantiomer" denotes that the compound comprises more than about 95%, 96%, 97%, 98%, 99%, 99.5, 99.6%, 99.7%, 99.8%, or 99.9% by weight of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid.

As used herein, and unless otherwise indicated, the terms "treat," "treating" and "treatment" refer to alleviating or reducing the severity of a disease or a symptom associated with the disease or condition being treated.

As used herein, "prevent", "prevention" and other forms of the word include the inhibition of onset or progression of a disease or disorder or a symptom of the particular disease or disorder. In some embodiments, patients with familial history of cancer are candidates for preventive regimens. Generally, in the context of cancer, the term "preventing" refers to administration of the drug prior to the onset of signs or symptoms of a cancer, particularly in patients at risk of cancer.

As used herein, and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" means an animal, typically a mammal, including a human being. As used herein, "patient" means a human subject.

As used herein, the term "cancer" includes, but is not limited to, solid tumors and blood-borne tumors. In some embodiments, the cancer may be a carcinoma or a sarcoma. In certain embodiments, the cancer is a hematologic malignancy, such as a leukemia, lymphoma (e.g., non-Hodgkin's lymphoma, Hodgkin's lymphoma), or a myeloma. In certain embodiments, the leukemia is chronic lymphocytic leukemia, chronic myeloid leukemia, acute lymphocytic leukemia, acute myelogenous leukemia and acute myeloblastic leukemia. In certain embodiments, the cancer comprises solid tumor. In certain embodiments, the cancer is a bladder cancer, brain cancer (e.g., astrocytoma, glioma, meningioma, neuroblastoma, or others), bone cancer (e.g., osteosarcoma), breast cancer, cervical cancer, cholangiocarcinoma, digestive tract cancer (e.g., oral, esophageal, stomach, colon or rectal cancer), head and neck cancer, leiomyosarcoma, liposarcoma, liver cancer, lung cancer (small cell or non-small cell), melanoma, mesothelioma, myeloma, nasopharyngeal cancer, neuroendocrine cancer, ovarian cancer, pancreatic cancer, prostate cancer, renal cancer, rhabdomyosarcoma, salivary gland cancer, skin cancer, spindle cell carcinoma, testicular cancer, thyroid cancer, or uterine cancer (e.g., endometrial cancer). In certain embodiments, the cancer can be relapsed following a previous therapy, or refractory to conventional therapy. In certain embodiments, the cancer can be disseminated or metastatic.

As used herein, the term "precancerous condition" means a condition, abnormal tissue growth, or lesion that tends or is likely to become cancerous. Precancerous conditions include, for example, actinic keratosis, adenomatous polyps of the colon, cervical dysplasia, and antecedent hematological disorders such as myelofibrosis, aplastic anemia, paroxysmal nocturnal hemoglobinuria, polycythemia vera, and myelodysplastic syndrome.

As used herein, the term "relapse" means a return of cancer signs or symptoms in a subject who has had a previous improvement or remission of cancer as a result of cancer therapy.

As used herein, the term "refractory" means that the cancer is or becomes resistant to a cancer therapy.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

As used herein and unless otherwise indicated, the term "pharmaceutically acceptable salt" includes, but is not limited to, a salt of an acidic or basic group that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means SNS-595 or a salt thereof, further including a stoichiometric or non-stoichiometric amount of water bound by non-covalent intermolecular forces. The hydrates of SNS-595 can be crystalline or non-crystalline.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate, and the like). The solvates of SNS-595 can be crystalline or non-crystalline.

As used herein, the transitional phrase "consisting essentially of" limits the scope of a claim to the specified materials and those that do not materially affect the basic and novel characteristic(s) of the claimed subject matter.

The terms "co-administration" and "in combination with" include the administration of two therapeutic agents (for example, SNS-595 or a composition provided herein and another anti-cancer agent or second agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "supportive care agent" refers to any substance that treats, prevents, manages, reduces, or avoids an adverse or unwanted effect of SNS-595 treatment.

5.2 Compounds and Compositions

In certain embodiments, provided herein are processes for preparation of SNS-595. In certain embodiments, the processes provided herein yield SNS-595 Substance. In certain embodiments, the processes provided herein yield compositions comprising SNS-595, N-desmethyl-SNS-595 and O-desmethyl-SNS-595. In certain embodiments, the processes provided herein yield compositions comprising substantially pure SNS-595. In certain embodiments, the processes provided herein yield compositions consisting essentially of SNS-595, N-desmethyl-SNS-595 and O-desmethyl-SNS-595. In certain embodiments, the processes provided herein yield compositions comprising SNS-595 and N-desmethyl-SNS-595. In certain embodiments, the processes provided herein yield compositions consisting essentially of SNS-595 and N-desmethyl-SNS-595. In certain embodiments, the processes provided herein yield compositions comprising SNS-595 and O-desmethyl-SNS-595. In certain embodiments, the processes provided herein yield compositions consisting essentially of SNS-595 and O-desmethyl-SNS-595. In certain embodiments, the processes provided herein yield compositions comprising SNS-595 and N,O-bisdesmethyl-SNS-595. In certain embodiments, the processes provided herein yield compositions consisting essentially of SNS-595 and N,O-bisdesmethyl-SNS-595. In certain embodiments, the processes provided herein yield compositions consisting essentially of SNS-595, N-desmethyl-SNS-595, O-desmethyl-SNS-595 and N,O-bisdesmethyl-SNS-595.

In certain embodiments, the compositions provided herein consist essentially of at least about 99.5% SNS-595 and less than about 0.5% of impurity by total weight of the composition, wherein each of the percentages is based upon total weight of the composition. In certain embodiments, the compositions provided herein consist essentially of at least about 99.5% SNS-595 and less than about 0.5% N-desmethyl-SNS-595 by total weight of the composition, wherein each of the percentages is based upon total weight of the composition. In one embodiment, provided herein is a composition consisting essentially of at least 99.9% SNS-595 and less than about 0.1% N-desmethyl-SNS-595. In one embodiment, provided herein is a composition consisting essentially of at least 99.95% SNS-595 and less than about 0.05% N-desmethyl-SNS-595. In one embodiment, the composition consists essentially of at least about 99.96%, at least about 99.97%, at least about 99.98%, at least about 99.99% SNS-595 by weight of the composition. In certain embodiments, the percentages of SNS-595 and N-desmethyl-SNS-595 in the composition are based upon total weight of the two components.

In certain embodiments, provided herein is a composition consisting essentially of SNS-595 and less than about 0.05% by weight of N-desmethyl-SNS-595. In one embodiment, the composition consists essentially of SNS-595 and less than about 0.01%, 0.02%, 0.03%, 0.04% or 0.05% of N-desmethyl-SNS-595 based upon total weight of the composition.

In certain embodiments, the compositions provided herein consist essentially of at least about 99.5% SNS-595 and less than about 0.5% O-desmethyl-SNS-595 by total weight of the composition, wherein each of the percentages is based upon total weight of the composition. In one embodiment, provided herein is a composition consisting essentially of at least about 99.9% SNS-595 and less than about 0.1% O-desmethyl-SNS-595. In one embodiment, provided herein is a composition consisting essentially of at least about 99.95% SNS-595 and less than about 0.05% O-desmethyl-SNS-595. In one embodiment, the composition consists essentially of at least about 99.96%, at least about 99.97%, at least about 99.98%, at least about 99.99% SNS-595 by weight of the composition. In certain embodiments, the percentages of SNS-595 and O-desmethyl-SNS-595 in the composition are based upon total weight of the two components.

In certain embodiments, provided herein is a composition consisting essentially of SNS-595 and less than about 0.05% by weight of O-desmethyl-SNS-595. In one embodiment, the composition consists essentially of SNS-595 and less than about 0.01%, 0.02%, 0.03%, 0.04% or 0.05% of O-desmethyl-SNS-595 based upon total weight of the composition.

In certain embodiments, the compositions provided herein consist essentially of SNS-595 and less than about 0.5%, 0.3%, 0.1%, 0.05%, 0.03% or 0.01% total N-desmethyl-SNS-595 and O-desmethyl-SNS-595 by total weight of the composition, wherein each of the percentages is based upon total weight of the composition.

In certain embodiments, the compositions consist essentially of at least about 99.5% SNS-595 and less than about 0.5%, 0.3%, 0.1%, 0.05%, 0.03% or 0.01% N,O-bisdesmethyl-SNS-595 by total weight of the composition, wherein each of the percentage is based upon total weight of the composition. In certain embodiments, the percentages of SNS-595 and N,O-bisdesmethyl-SNS-595 in the composition are based upon total weight of the two components.

In certain embodiments, the compositions provided herein consist essentially of SNS-595 and less than about 0.5%, 0.3%, 0.1%, 0.05%, 0.03% or 0.01% total N-desmethyl-SNS-595, O-desmethyl-SNS-595 and N,O-bisdesmethyl-SNS-595 by total weight of the composition, wherein each of the percentages is based upon total weight of the composition. In certain embodiments, the percentages of SNS-595, N-desmethyl-SNS-595, O-desmethyl-SNS-595 and N,O-bisdesmethyl-SNS-595 in the composition are based upon total weight of the four components.

In certain embodiments, SNS-595 Substance provided herein can be synthesized on a process scale.

In certain embodiments, SNS-595 Substance provided herein is useful in the methods of treating, preventing or managing one or more cancers in a subject.

In one embodiment, provided herein are methods of treatment, prevention, or amelioration of one or more cancers comprising administering SNS-595 Substance.

Also provided herein are compounds of formula 5A and 5B and methods of preparing the compounds.

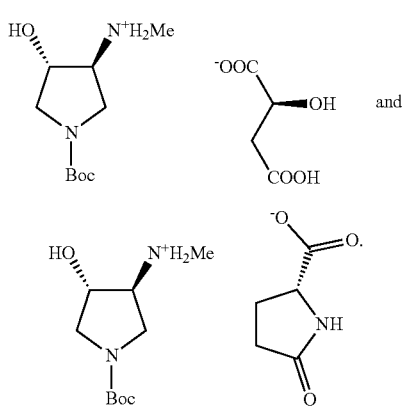

In certain embodiments, Compound 5A and Compound 5B are useful as intermediates in synthesis of SNS-595.

5.3 Methods of Preparation

SNS-595 can be prepared from (3S,4S)-4-methoxy-N-methylpyrrolidin-3-amine.2TsOH and 7-chloro-4-oxo-1-thiazol-2-yl-1,4-dihydro-[1,8]naphthyridine-3-carboxylic acid ethyl ester as described in Example 3.

In one embodiment, the chemical process for preparation of SNS-595 provided herein yields SNS-595 Substance consisting essentially of at least about 99.5% SNS-595, including less than about 0.5% of impurity. In another embodiment, the chemical process yields SNS-595 Substance consisting essentially of at least about 99.7% SNS-595, including about 0.3% of impurity, at least about 99.9% SNS-595 and less than about 0.1% of impurity, at least about 99.95% SNS-595 and less than about 0.05% of impurity, at least about 99.97% SNS-595 and less than about 0.03% of impurity, at least about 99.98% SNS-595 and less than about 0.02% of impurity or at least about 99.99% SNS-595 and less than about 0.01% of impurity.

In certain embodiments, the process provided herein yields SNS-595 Substance consisting essentially of SNS-595, including less than about 0.1% of N-desmethyl-SNS-595. In one embodiment, the process provided herein yields SNS-595 Substance consisting essentially of SNS-595, including less than about 0.01%, 0.02%, 0.03%, 0.04% or 0.05% of N-desmethyl-SNS-595 based upon total weight of the composition.

In certain embodiments, the process provided herein yields SNS-595 Substance consisting essentially of SNS-595, including less than about 0.1% of O-desmethyl-SNS-595. In one embodiment, the process provided herein yields SNS-595 Substance consisting essentially of SNS-595, including less than about 0.01%, 0.02%, 0.03%, 0.04% or 0.05% of O-desmethyl-SNS-595 based upon total weight of the composition.

In certain embodiments, the process provided herein yields SNS-595 Substance consisting essentially of SNS-595, including less than about 0.1% of total N-desmethyl-SNS-595 and O-desmethyl-SNS-595. In one embodiment, the process provided herein yields SNS-595 Substance consisting essentially of SNS-595, including less than about 0.01%, 0.02%, 0.03%, 0.04% or 0.05% of total N-desmethyl-SNS-595 and O-desmethyl-SNS-595 based upon total weight of the composition.

In certain embodiments, the process provided herein yields SNS-595 Substance consisting essentially of SNS-595, including less than about 0.1% of N,O-bisdesmethyl-SNS-595. In one embodiment, the process provided herein yields SNS-595 Substance consisting essentially of SNS-595, including less than about 0.01%, 0.02%, 0.03%, 0.04% or 0.05% of N,O-bisdesmethyl-SNS-595 based upon total weight of the composition.

Several methods for preparation of (3S,4S)-4-methoxy-N-methylpyrrolidin-3-amine.2TsOH are reported in the literature (see, U.S. Pat. No. 5,817,669, WO 2007/146335, Tsuzuki et al., *J. Med. Chem.*, 47:2097-2106, 2004 and Tomita et al., *J. Med. Chem.*, 45: 5564-5575, 2002). These processes can provide products contaminated by significant levels of impurities including N-desmethyl- and O-desmethyl-analogs of Compound 8 and others. One such method is illustrated in Scheme 3.

Scheme 3

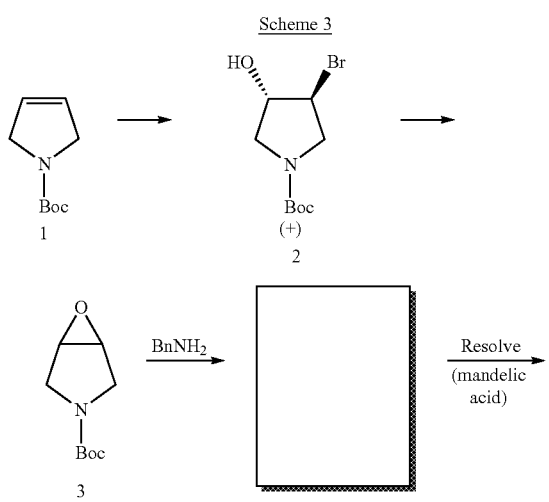

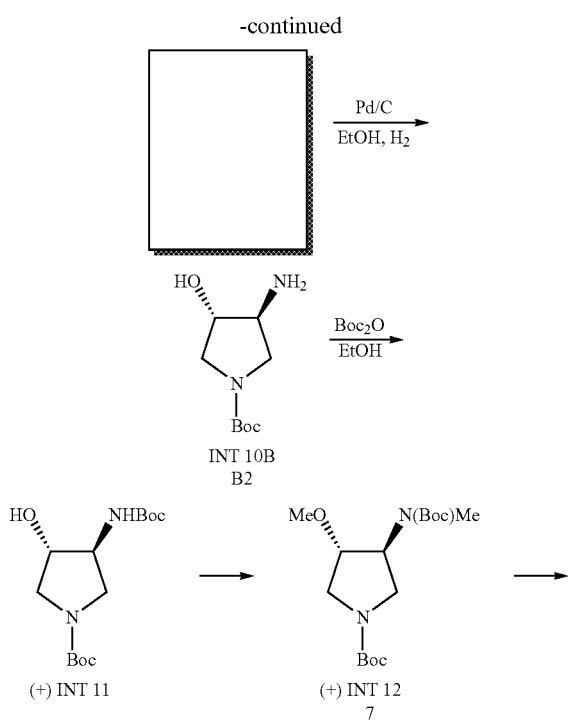

As reported previously, for example, see, WO 2007/146335, Tsuzuki et al., *J. Med. Chem.*, 47:2097-2106, 2004 and Tomita et al., *J. Med. Chem.*, 45: 5564-5575, 2002, during the scale up of this process, up to 1.5% of 4-methoxypyrrolidin-3-amine, i.e., N-desmethyl-compound 8, impurity was observed, presumably as a result of incomplete methylation of INT11 in the INT12 step. This impurity is converted during the synthesis of SNS-595 to the known impurity, N-desmethyl-SNS-595 as shown in Scheme 4.

Scheme 4

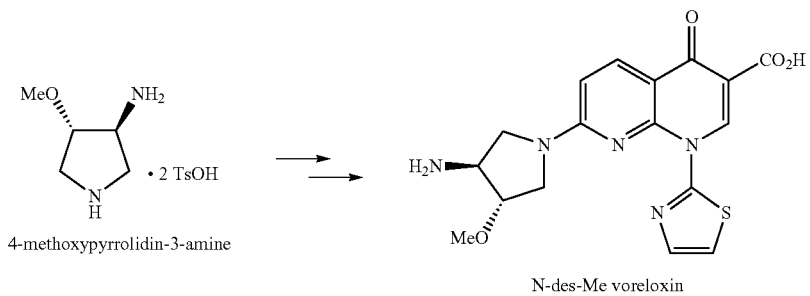

4-methoxypyrrolidin-3-amine

N-des-Me voreloxin

In addition, the process was not reproducible and the yield and amount of impurities were impacted by small variations in temperature and reaction times. Dimeric and trimeric impurities (which were difficult to remove) were formed at slightly elevated temperatures and longer hold times. In many instances, the levels of impurities were so high and the yield so low that the product was difficult to crystallize.

Table 1 provides impurity profile for synthetic route illustrated in Scheme 3.

TABLE 1

Impurity profile of Compound 8 prepared according to Scheme 3

| Batch Size (output) | N,O- (%) | O- (%) | N- (%) | Compound 8 (%) | Other impurities (%) |
|---|---|---|---|---|---|
| ~0.1 kg | 0.0 | 0.06 | 0.31 | 96.6 | 0.48, 0.66 |
| ~1.28 kg | 0.09 | 0.99 | 0.83 | 94.7 | 0.57, 1.16 |
| ~14 kg | 0.10 | 0.28 | 1.46 | 96.1 | 0.41, 0.25 |

In Table 1, "N,O-" refers to N,O-bis-desmethyl-Compound 8, having the formula:

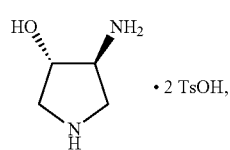

"O-" refers to O-desmethyl-Compound 8, having the formula:

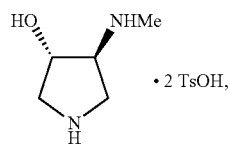

"N-" refers to N-desmethyl-Compound 8, having the formula:

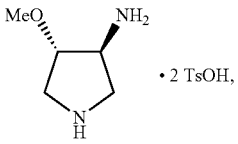

and

"NR" means that data were not reported.

In certain embodiments, provided herein are processes for the preparation of SNS-595 designed to reduce or eliminate incomplete methylation that results in the N-desmethyl-Compound 8 impurity. An exemplary process is depicted in Scheme 1.

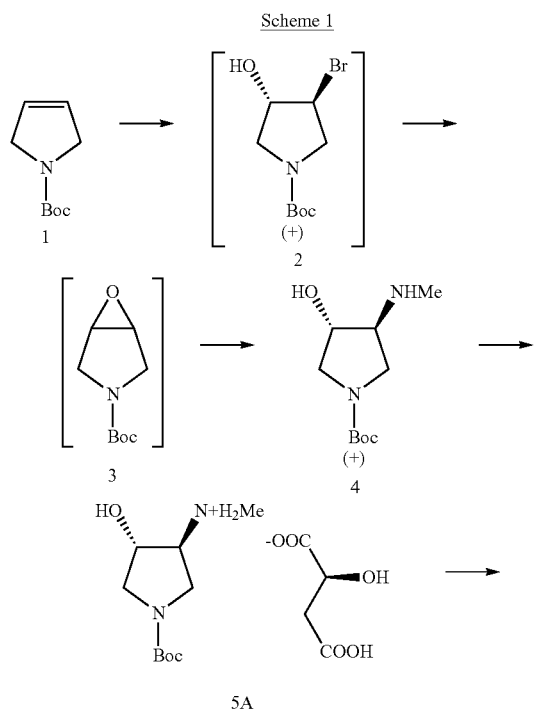

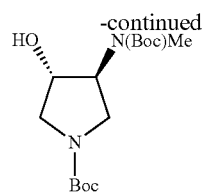

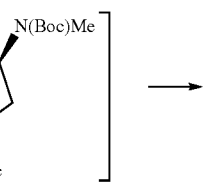 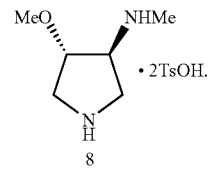

In Scheme 1, the N-methyl group is introduced not by methylation, but by nucleophilic opening of the epoxide by methylamine, thereby eliminating the impurities resulting from incomplete methylation.

In certain embodiments, methylamine does not contain detectable quantity of ammonia. In such embodiments, Compound 4 does not contain the corresponding N-des-methyl impurity. In certain embodiments, methylamine contains less than about 1%, 0.9%, 0.8%, 0.7%, 0.6%, 0.5%, 0.4%, 0.3%, 0.2% or 0.1% or less ammonia.

Any impurity present can be purged by crystallizations at Compound 4, Compound 5A, and/or Compound 6 steps.

As illustrated in Scheme 1, intermediate Compound 4 can be prepared by a process from commercially available Boc-3-pyrroline (Compound 1), see, e.g., *Tetrahedron Asymmetry*, 12 (2002) 2989-2997.

Intermediate Compound 4 can be resolved by forming a complex with a chiral acid. Any chiral acid deemed suitable by one of skill in the art can be used. Exemplary chiral acids include, but are not limited to malic acid, pyroglutamic acid (PGA), tartaric acid, di-p-toluoyltartaric acid (DTTA), camphor sulfonic acid (CSA), and mandelic acid.

In one embodiment, the chiral acid is L-(−)-malic acid or L-(−)-pyroglutamic acid. In one embodiment, L-(−)-malic acid reacts with Compound 4 to form Compound 5A. In one embodiment, L-(−)-pyroglutamic acid reacts with Compound 4 to form Compound 5B. In certain embodiments, about 0.25 to 2 equivalents of the chiral acid is used. In one embodiment, about 0.5 to 1.5 equivalents of the chiral acid is used. In one embodiment, about 0.9 to 1.1 equivalents of the chiral acid is used. In certain embodiments, about 0.25 to 2 equivalents of L-(−)-malic acid is used. In one embodiment, about 0.5 to 1.5 equivalents of L-(−)-malic acid is used. In one embodiment, about 0.9 to 1.1 equivalents of L-(−)-malic acid is used.

In one embodiment, L-(−)-malic acid produces the L-(−)-malate salt, Compound 5A, in greater than about 98%, 99%, 99.3%, 99.5%, 99.7%, 99.8% or 99.9% enantiomeric excess. In one embodiment, L-(−)-malic acid produces the L-(−)-malate salt, Compound 5A, in up to about 100% enantiomeric excess.

The secondary amine in Compound 5A is protected by a protecting group. Any suitable protecting group, including benzyl, benzyloxycarbonyl, acetyl, phenylcarbonyl and t-butoxycarbonyl can be used. The methylation of free hydroxyl group is carried out with a methylating agent, such as dimethylsulfate, methyl p-toluenesulfonate, or methanesulfonate. Compound 8 is obtained by removal of the protecting groups under acidic conditions. Suitable deprotecting agents include p-toluene sulfonic acid monohydrate. In Scheme 1, the secondary amine in Compound 5A is protected with t-butyloxy carbonyl group, to obtain Compound 6, by treatment with Boc$_2$O. Compound 6 is then methylated using methylating conditions, such as potassium hexamethyldisilazane (KHMDS) and Me$_2$SO$_4$ to give Compound 7. The crude product is deprotected under previously known (see, Scheme 2) conditions to give Compound 8 in consistently high purity and yield.

As described in Examples 1 and 3, this route can be scaled up successfully to produce laboratory scale batches (100 g to 1 kg scale) and cGMP batches of Compound 8 on ~16 kg scale from commercially available Boc-3-pyrroline (Compound 1). All batches in the examples had little N-desmethyl impurity (Table 2). Other related substances were also below quantitation limits of about 0.1%. The enantiomeric purity (determined by HPLC) of Compound 8 was also high (>99.8% ee). No new impurities were identified in the development or scale up batches.

TABLE 2

Impurity profile of Compound 8 prepared according to Scheme 1

| Batch Size | HPLC area % | | | | |
|---|---|---|---|---|---|
| (output) | N,O- | O- | N- | Compound 8 | % (R, R) |
| 66 g | ND | ND | ND | 100.0 | 0.0 |
| 65 g | ND | ND | ND | 100.0 | 0.0 |
| 68 g | ND | ND | ND | 100.0 | 0.0 |
| 0.75 kg | ND | ND | ND | 99.8 | 0.0 |
| 10.2 kg | ND | 0.03 | 0.03 | 99.7 | 0.08 |
| 12.2 kg | ND | ND | ND | 99.7 | 0.03 |
| 12.1 kg | ND | ND | 0.01 | 99.7 | 0.09 |

ND refers to Not detected

In certain embodiments, enantiomeric enrichment occurs during the crystallization of Compound 8. In certain embodiments, the chiral purity of Compound 8 can be enhanced by additional crystallization.

In certain embodiments, Compound 5A with as low as 90% ee is carried forward to produce Compound 8 with >99.5% ee.

Incomplete methylation of Compound 6 results in O-desmethyl-Compound 6 as a process impurity. The level of this impurity was below quantitation limits (<0.1%) in the batches shown in Table 2. Two successful approaches were evaluated to control this impurity in the process:

a. In-process control in the methylation step (conversion of Compound 6 to Compound 7). Current in-process control limits are <2% Compound 6 by HPLC. When batches of Compound 7 containing up to 2% Compound 6 were carried through Compound 8 and isolation, the levels of O-desmethyl-Compound 6 were below 0.1%.

b. Purging of O-desmethyl-Compound 8 was shown to occur during the crystallization of Compound 8. Therefore, O-desmethyl-Compound 8, if formed, can be reduced by additional crystallization.

Based on the methods described, the synthetic route illustrated in Scheme 1 and described in Example 1 is robust for scale up, and can produce Compound 8 of consistently high chemical and enantiomeric purity. Specifically, this route produces Compound 8 with little, if any, of previously known impurities (N-desmethyl-Compound 8 and O-desmethyl-Compound 8) and produces no new impurities.

Compound 8 produced in Scheme 1 can be further reacted with 7-chloro-4-oxo-1-thiazol-2-yl-1,4-dihydro-[1,8]naphthyridine-3-carboxylic acid ethyl ester to obtain SNS-595 as described in Example 3. Full analytical testing of SNS-595 obtained by the process described herein showed that no detectable new impurities were formed.

In certain embodiments, SNS-595 produced by the methods provided herein contains less than about 0.1% N-desmethyl-SNS-595 and O-desmethyl-SNS-595. In certain embodiments, SNS-595 produced by the methods provided herein contains less than about 0.1% N-desmethyl-SNS-595. In certain embodiments, SNS-595 produced by the methods provided herein contains less than about 0.09, 0.08, 0.07, 0.06, 0.05, 0.04, 0.03, 0.02 or 0.01% N-desmethyl-SNS-595. In certain embodiments, SNS-595 produced by the methods provided herein contains less than about 0.1% O-desmethyl-SNS-595. In certain embodiments, SNS-595 produced by the methods provided herein contains less than about 0.09, 0.08, 0.07, 0.06, 0.05, 0.04, 0.03, 0.02 or 0.01% O-des-methyl-SNS-595. In certain embodiments, SNS-595 produced by the methods provided herein contains less than about 0.1% total N-desmethyl-SNS-595 and O-desmethyl-SNS-595. In certain embodiments, SNS-595 produced by the methods provided herein contains less than about 0.09, 0.08, 0.07, 0.06, 0.05, 0.04, 0.03, 0.02 or 0.01% total N-desmethyl-SNS-595 and O-desmethyl-SNS-595.

In certain embodiments, the methods provided herein are useful in preparing SNS-595 Substance on a process scale. In certain embodiments, the methods provided herein are useful in preparing 0.1, 0.3, 0.5, 1, 2, 3, 4, 5, 7, 10, 15, 20, 25, 50, and 100 kg or more SNS-595 Substance.

5.4 Methods of Use

Provided herein are methods of treating, preventing, and/or managing various cancers, comprising administering SNS-595 Substance prepared according to the processes described herein. In certain embodiments, the methods encompass administering substantially pure SNS-595. Examples of cancers include solid tumors and hematologic cancers. The methods provided herein may also be used for treatment or prevention of precancerous conditions.

Accordingly, provided herein are methods of treating, managing, or preventing cancers or precancerous conditions, comprising administering a dose of about 10-100 mg/m$^2$ of SNS-595 Substance to a subject in need of such treatment, management or prevention. The cancer types include, but are not limited to, ovarian cancer, breast cancer, small cell lung cancer and non-small cell lung cancer. In one embodiment, the cancer is relapsed. In one embodiment, the cancer is refractory. In one embodiment, the cancer is resistant to conventional therapy. In one embodiment, the cancer is ovarian cancer resistant to conventional therapy. In one embodiment, the cancer is platinum-resistant epithelial ovarian cancer.

In one embodiment, the methods provided herein encompass treating, preventing or managing various types of leukemia in a subject, such as chronic lymphocytic leukemia (CLL), chronic myelocytic leukemia (CML), acute lymphoblastic leukemia (ALL), and acute myelogenous leukemia (AML), or acute myeloblastic leukemia (AML).

In one embodiment, provided herein are methods for treatment of acute myeloid leukemia. In one embodiment, the methods for treatment of refractory or relapsed acute myeloid leukemia.

The methods provided herein encompass treating patients who have been previously treated for cancer, but are non-responsive to standard therapies, as well as those who have not previously been treated. Also encompassed are methods of treating patients regardless of patient's age, although some diseases or disorders are more common in certain age groups. Further provided are methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

4.5 Dosages

In certain representative embodiments, the method of treating, preventing or managing cancers provided herein comprises administering to a patient on the basis of body surface area, a dose of about 10 mg/m$^2$-100 mg/m$^2$ of SNS-595 Substance. In certain representative embodiments, the method of treating, preventing or managing cancers provided herein comprises administering to a patient on the basis of body surface area, a dose of about 10 mg/m$^2$-110 mg/m$^2$ of SNS-595 Substance. In certain embodiments, the methods encompass administering substantially pure SNS-595. In another embodiment, the method of comprises administering a dose of about 20 mg/m$^2$-90 mg/m$^2$ of SNS-595 Substance. In another embodiment, the method comprises administering a dose of about 40 mg/m$^2$-80 mg/m$^2$ of SNS-595 Substance. In another embodiment, the method comprises administering a dose of about 30 mg/m$^2$-50 mg/m$^2$ of SNS-595 Substance. In another embodiment, the method comprises administering a dose of about 50 mg/m$^2$-110 mg/m$^2$ of SNS-595 Substance.

The skilled practitioner in treating cancer typically employs a dosage unit that enables approximation of the subject's exposure to the active ingredient being administered. For example, the dosage unit used may approximate exposure based on a calculation of body surface area. Body surface area (BSA) calculations for a human subject can be calculated, for example, using the Mosteller formula:

$$BSA\ (m^2)=[(\text{height (cm)}\times\text{body mass (kg)})/3600]^{1/2}.$$

The most common such dosage unit is milligrams of active compound per square meter of body surface area (mg/m$^2$).

The administered dose of the SNS-595 can be expressed in units other than mg/m$^2$. For example, doses can be expressed as milligrams of active compound per kilogram of body mass (mg/kg). One of ordinary skill in the art would readily know how to convert a patient dose from mg/m$^2$ to mg/kg, given the height and/or body mass of the patient (see, http:///www-.fda.gov/cder/cancer/animalframe.htm). For example, a dose of 1 mg/m$^2$-30 mg/m$^2$ for a 65 kg human is approximately equal to 0.026 mg/kg-0.79 mg/kg. Other dosage units may also be employed.

In certain embodiments, the administered dose of SNS-595 Substance provided herein can be delivered as a single bolus (e.g., intravenous injection) or over a longer period (e.g., continuous infusion or periodic bolus doses). Administration of SNS-595 Substance may be repeated until the subject experiences stable disease or regression or until the subject experiences disease progression or unacceptable toxicity. Stable disease or lack thereof is determined by methods known in the art, such as evaluation of symptoms, physical examination, and other commonly accepted parameters.

The amount of SNS-595 Substance administered according to the methods provided herein will depend on various factors, such as the overall health of the patient being treated, the severity of the disorder or symptom of the disorder, the active ingredient being administered, the manner of administration, the frequency of administration, other medications present, and the judgment of the prescribing physician. The amount to be administered can be empirically determined by the physician.

In some embodiments, the frequency of administration is in the range of about a daily dose to about a monthly dose. In certain embodiments, administration is once per day, once every other day, once per week, twice per week, three times per week, once every two weeks, once every three weeks, or once every four weeks. In one embodiment, the pharmaceutical composition provided herein is administered once per week for three weeks. In another embodiment, the pharmaceutical composition provided herein is administered once per week for three weeks. In one embodiment, the pharmaceutical composition provided herein is administered once every three weeks. In another embodiment, the pharmaceutical composition provided herein is administered once every four weeks.

In certain embodiments, SNS-595 Substance provided herein is administered to a patient in one or more cycles of administration. Cycling therapy involves the administration of one or more doses of SNS-595 Substance, followed by a period of rest, and repeating this administration/rest cycle. Cycling therapy can reduce the development of resistance to one or more of the therapies, avoid or reduce the side effects of one or more of the therapies, and/or improve the efficacy or duration of the treatment.

Consequently, in one embodiment, SNS-595 Substance provided herein is administered once per week, in a single dose or in divided doses, in a three- to six-week cycle with a rest period of about 1 to about 30 days between doses. In some embodiments, the waiting period is 14 days, with the first dose given on day 1 and the next dose given on day 15. Treatment in such cases may thus be said to be using a "14-day cycle." In some embodiments, the doses may be given 28 days apart, i.e., a 28-day cycle.

In another embodiment, the dosing method comprises a cycle wherein the cycle comprises administering a dose of SNS-595 Substance to a patient once per week for three weeks followed by a period of at least 14 days in which no compound or composition is administered to the patient and wherein the cycle is repeated a plurality of times. In another embodiment, the period in which no compound or composition is administered is 18 days. In another embodiment, the period in which no compound or composition is administered is 21 days. In another embodiment, the period in which no compound or composition is administered is 28 days. The frequency, number and length of dosing cycles can be increased or decreased.

In one embodiment, the method provided herein comprises: i) administering a dose of about 40-80 mg/m$^2$ of SNS-595 Substance provided herein to a patient; ii) waiting a period of at least six days where the patient is not administered any SNS-595 Substance; and iii) administering another dose of about 40-80 mg/m$^2$ of SNS-595 Substance to the patient. In one embodiment, steps ii)-iii) are repeated a plurality of times.

In one embodiment, the method provided herein comprises: i) administering a dose of about 30-50 mg/m$^2$ of SNS-595 Substance provided herein to a patient; ii) waiting a period of at least six days in which the patient is not administered any SNS-595 Substance; and iii) administering another dose of about 30-50 mg/m$^2$ of SNS-595 Substance to the patient. In one embodiment, steps ii)-iii) are repeated a plurality of times.

In one embodiment, the method provided herein comprises: i) administering a dose of about 50-110 mg/m$^2$ of SNS-595 Substance provided herein to a patient; ii) waiting a period of at least six days where the patient is not administered any SNS-595 Substance; and iii) administering another dose of about 50-110 mg/m² of SNS-595 Substance to the patient. In one embodiment, steps ii)-iii) are repeated a plurality of times.

In another embodiment, the method comprises administering a dose of about 40 mg/m², about 45 mg/m², about 48 mg/m², about 50 mg/m², about 60 mg/m², about 72 mg/m², about 75 mg/m², about 80 mg/m², or about 90 mg/m² of SNS-595 Substance provided herein, in each of the foregoing steps i) and iii).

In another embodiment, provided herein is a method for treatment of solid tumors comprising administering a dose of about 48 mg/m² of SNS-595 Substance provided herein to a patient once every three weeks. In another embodiment, provided herein is a method for treatment of such solid tumors comprising administering a dose of about 60 mg/m² of SNS-595 Substance provided herein to a patient once every four weeks. In another embodiment, provided herein is a method for treatment of such solid tumors comprising administering a dose of about 75 mg/m² of SNS-595 Substance provided herein to a patient once every four weeks. In such embodiments, the method may be used for treatment of ovarian cancer, such as platinum-resistant epithelial ovarian cancer.

In another embodiment, provided herein is a method for treatment of leukemia, comprising administering a dose of about 50 mg/m² of SNS-595 Substance provided herein to a patient once per week. In another embodiment, provided herein is a method for treatment of leukemia, comprising administering a dose of about 60 mg/m² of SNS-595 Substance provided herein to a patient once per week. In another embodiment, provided herein is a method for treatment of leukemia comprising administering a dose of about 72 mg/m² of SNS-595 Substance provided herein to a patient once per week. In another embodiment, provided herein is a method for treatment of leukemia comprising administering a dose of about 72 mg/m² of SNS-595 Substance provided herein to a patient once per week for two weeks. In another embodiment, provided herein is a method for treatment of leukemia comprising administering a dose of about 72 mg/m² of SNS-595 Substance provided herein to a patient once per week for three weeks. In another embodiment, provided herein is a method for treatment of leukemia comprising administering a dose of about 90 mg/m² of SNS-595 Substance provided herein to a patient once per week for three weeks. In another embodiment, provided herein is a method for treatment of leukemia, comprising administering a dose of about 40 mg/m² of SNS-595 Substance provided herein to a patient twice per week. In one embodiment, the method is for treatment of acute myeloid leukemia.

In certain embodiments, the dosing method comprises administering to a subject a dose of SNS-595 Substance twice per week for two weeks (dosing on days 1, 4, 8 and 11). In another embodiment, the dosing method comprises administering a once-per-week dose of SNS-595 Substance to a subject. In another embodiment, the dosing method comprises administering a dose of SNS-595 Substance to a subject once every two weeks. In another embodiment, the dosing method comprises administering a dose of SNS-595 Substance to a subject once every three weeks. In another embodiment, the dosing method comprises administering a dose of SNS-595 Substance to a subject once every four weeks.

In one embodiment, a dose of about 40-80 mg/m² of SNS-595 Substance is administered to a patient once every three weeks wherein the three-week period comprises a treatment cycle and the treatment cycle is repeated at least one time. In another embodiment, the method comprises administering a dose of about 40-80 mg/m² of SNS-595 Substance to a patient once every four weeks wherein the four-week period comprises a treatment cycle and the treatment cycle is repeated at least one time. In another embodiment, the method comprises administering a dose of about 48 mg/m² of SNS-595 Substance to a patient once every three weeks wherein the three-week period comprises a treatment cycle and the treatment cycle is repeated at least one time. In another embodiment, the method comprises administering a dose of about 60 mg/m² of SNS-595 Substance to a patient once every four weeks wherein the four-week period comprises a treatment cycle and the treatment cycle is repeated at least one time. In another embodiment, the method comprises administering a dose of about 75 mg/m² of SNS-595 Substance to a patient once every four weeks wherein the four-week period comprises a treatment cycle and the treatment cycle is repeated at least one time.

In one embodiment, the method comprises administering a dose of about 40-80 mg/m² of SNS-595 Substance to a patient once per week wherein the one-week period comprises a treatment cycle and the treatment cycle is repeated at least three times. In one embodiment, the method comprises administering a dose of about 50-110 mg/m² of SNS-595 Substance to a patient once per week wherein the one-week period comprises a treatment cycle and the treatment cycle is repeated at least three times. In another embodiment, the method comprises administering a dose of about 30-50 mg/m² of SNS-595 Substance to a patient twice per week wherein the one-week period comprises a treatment cycle and the treatment cycle is repeated at least two times. In another embodiment, the dose is about 50 mg/m² of SNS-595 Substance once per week wherein the one-week period comprises a treatment cycle and the treatment cycle is repeated at least three times. In another embodiment, the dose is about 60 mg/m² of SNS-595 Substance once per week wherein the one-week period comprises a treatment cycle and the treatment cycle is repeated at least three times. In another embodiment, the dose is about 72 mg/m² of SNS-595 Substance once per week wherein the one-week period comprises a treatment cycle and the treatment cycle is repeated at least three times. In another embodiment, the dose is about 90 mg/m² of SNS-595 Substance once per week wherein the one-week period comprises a treatment cycle and the treatment cycle is repeated at least three times. In another embodiment, the method comprises administering a dose of 40 mg/m² of SNS-595 Substance to a patient twice per week wherein the one-week period comprises a treatment cycle and the treatment cycle is repeated at least two times. In certain embodiments, the methods encompass administering substantially pure SNS-595.

All methods and dosages described herein apply to the treatment or prevention of cancer or precancerous condition.

4.6 Second Active Agents

It will also be appreciated that SNS-595 Substance and pharmaceutical compositions comprising SNS-595 Substance prepared according to the method described herein can be employed in complementary combination therapies with other active agents or medical procedures. In certain embodiments, substantially pure SNS-595 is used in combination therapies.

SNS-595 Substance and pharmaceutical compositions thereof can be administered concurrently with, prior to, or subsequent to, one or more other desired active agents or medical procedures. The particular combination of therapies (agents or procedures) to employ in a combination regimen will take into account compatibility of the desired therapeutics and/or procedures and the desired therapeutic effect to be achieved. It will also be appreciated that the therapies employed may achieve a desired effect for the same disorder (for example, SNS-595 Substance may be administered concurrently with another active agent used to treat the same disorder), or they may achieve different effects (e.g., control of any adverse effects). Non-limiting examples of such agents and procedures include surgery, radiotherapy (e.g., gamma-radiation, neutron beam radiotherapy, electron beam radiotherapy, proton therapy, brachytherapy, and systemic radioisotopes), endocrine therapy, biologic response modifiers (interferons, interleukins, and tumor necrosis factor (TNF) to name a few examples), hyperthermia and cryotherapy, agents to attenuate any adverse effects (e.g., antiemetic agents), and other approved chemotherapeutic anticancer agents.

Examples of chemotherapeutic anticancer agents that may be used as second active agents in combination with SNS-595 Substance include, but are not limited to, alkylating agents (e.g., mechlorethamine, chlorambucil, cyclophosphamide, melphalan, ifosfamide), antimetabolites (e.g., methotrexate), aurora kinase inhibitors (e.g., SNS-314), purine antagonists and pyrimidine antagonists (e.g., 6-mercaptopurine, 5-fluorouracil (5-FU), cytarabine (Ara-C), gemcitabine), spindle poisons (e.g., vinblastine, vincristine, vinorelbine, paclitaxel), podophyllotoxins (e.g., etoposide, irinotecan, topotecan), antibiotics (e.g., doxorubicin, daunorubicin, bleomycin, mitomycin), nitrosoureas (e.g., carmustine, lomustine), inorganic ions (e.g., platinum complexes such as cisplatin, carboplatin), enzymes (e.g., asparaginase), hormones (e.g., tamoxifen, leuprolide, flutamide, and megestrol), topoisomerase II inhibitors or poisons, EGFR (Her1, ErbB-1) inhibitors (e.g., gefitinib), antibodies (e.g., bevacizumab, rituximab), IMIDs (e.g., thalidomide, lenalidomide), various targeted agents (e.g., HDAC inhibitors such as vorinostat), Bcl-2 inhibitors, VEGF inhibitors, proteasome inhibitors (e.g., bortezomib), cyclin-dependent kinase (cdk) inhibitors (e.g., SNS-032, seliciclib), and dexamethasone.

In one embodiment, examples of chemotherapeutic anticancer agents that may be used as second active agents in combination with SNS-595 Substance include, docetaxel, vinorelbine, capecitabine, doxorubicin, gosereli, zoledronic acid, paclitaxel, pamidronate, anastrozole, exemestane, cyclophosphamide, epirubicin, fulvestrant, letrozole, gemcitabine, leuprolide, filgrastim (G-CSF or granulocyte colony stimulating factor), toremifene, tamoxifen, pegfilgrastim, epoetin alfa and darbepoetin alfa. In certain embodiments, SNS-595, in combination with these second agents, can be used for the treatment of breast cancer.

Some specific anticancer agents that can be used in combination with SNS-595 Substance include, but are not limited to: cytarabine, carboplatin, cisplatin, gemcitabine, and combinations of any two or more thereof.

4.7 Combination Therapy with a Second Active Agent

In certain embodiments, the method provided herein comprises administering SNS-595 Substance or pharmaceutical compositions provided herein in combination with one or more second active agents, and/or in combination with radiation therapy or surgery. In certain embodiments, the methods encompass administering substantially pure SNS-595 in combination with one or more second active agents, and/or in combination with radiation therapy or surgery.

The administration of SNS-595 Substance and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference, 1755-1760 (56$^{th}$ ed., 2002) (hereinafter "Physicians' Desk Reference").

In one embodiment, the second active agent is administered intravenously or subcutaneously and once or twice daily in an amount of from about 1 to about 1,000 mg, from about 5 to about 500 mg, from about 10 to about 375 mg or from about 50 to about 200 mg.

In another embodiment, provided herein are methods of treating, preventing and/or managing hematologic malignancies, which comprise administering SNS-595 Substance provided herein in conjunction with (e.g., before, during or after) conventional therapy including, but not limited to, surgery, immunotherapy, biological therapy, radiation therapy or other non-drug based therapy presently used to treat, prevent or manage cancer.

In one embodiment, SNS-595 Substance can be administered in an amount of about 10-100 mg/m$^2$, 20-90 mg/m$^2$, 40-80 mg/m$^2$, or 30-50 mg/m$^2$, alone or in combination with a second active agent disclosed herein (see, e.g., section 4.6), prior to, during, or after the use of conventional therapy.

In one embodiment, the second agent is selected from the group consisting of cytarabine, carboplatin, cisplatin, gemcitabine, and combinations any two or more thereof.

In certain embodiments, SNS-595 Substance may be administered in combination with about 5 to 1500 mg/m$^2$ of cytarabine. For example, one embodiment includes continuous daily administration of cytarabine at a dose of about 200 to 400 mg/m$^2$. The administration of cytarabine can be made by intravenous infusion, intravenous push, bolus injection or subcutaneous injection. In certain embodiments, the administration of cytarabine is daily, e.g., for 5 days, while the administration of SNS-595 occurs once or twice per week. As discussed herein, the administration of SNS-595 and cytarabine as set forth above in a week is considered a weekly cycle. The methods encompass performing one weekly cycle, waiting a period of one week to several weeks where neither cytarabine nor SNS-595 is given then repeating a weekly cycle. The methods also contemplate repeating the weekly cycles continuously, for example, for 4 weeks or 28 days. In addition, the methods contemplate repeating the cycle for several cycles, waiting a period of a week to several weeks where neither cytarabine nor SNS-595 Substance is given then repeating one or more cycles. Finally, the methods provide administration of a SNS-595 Substance/cytarabine weekly cycle followed by a cycle of only cytarabine or SNS-595.

Also provided are methods in which the daily cytarabine is administration is at a dose of about 5-50 mg/m$^2$ and where SNS-595 Substance is administered once per week or twice per week. For example, the cytarabine may be administered daily for 10 days, and SNS-595 Substance may be administered on a schedule of once per week for three weeks, or twice per week for two weeks.

Use of SNS-595 Substance with cytarabine may be employed, for example, in the treatment of leukemias, such as acute myeloid leukemia. In one exemplary embodiment, a treatment cycle may be used that comprises administering to a patient about 20-90 mg/m$^2$ or about 40-80 mg/m$^2$ of SNS-595 Substance on days 1 and 4 of a 28-day cycle, and administering to the patient about 400 mg/m$^2$ of cytarabine on days 1-5 of the cycle. In such a method, the doses of SNS-595 Substance may be administered by intravenous (IV) injection, and the doses of cytarabine by continuous intravenous (CIV) infusion. In an alternative exemplary embodiment, a patient having AML may be treated using a treatment cycle comprising administering to the patient about 20-90 mg/m$^2$ or about 40-80 mg/m$^2$ of SNS-595 Substance on days 1 and 4, and administering to the patient about 1000 mg/m$^2$/day on days 1-5. In such a method, the doses of SNS-595 Substance may be administered by IV injection, and the doses of cytarabine by IV infusion over two hours.

In one embodiment, the combination therapy comprises administering SNS-595 Substance and carboplatin. In one embodiment, the combination therapy comprises administering SNS-595 Substance and cisplatin. In one embodiment, the combination therapy comprises administering SNS-595 Substance and gemcitabine.

In one embodiment, the methods provided include the administration of SNS-595 Substance in combination with about 5 mg/m$^2$ to about 200 mg/m$^2$ cisplatin. For example, one embodiment includes administration of cisplatin at a dose of about 50 or 70 mg/m$^2$ once every 3 to 4 weeks. One embodiment includes administration of cisplatin at a dose of about 50 or 70 mg/m$^2$ once every 3 weeks. Another embodiment includes administration of cisplatin at a dose of about 75 or 100 mg/m$^2$ once every 3 weeks. In another embodiment, administration of cisplatin is at a dose of about 20 mg/m$^2$ daily for up to 5 days. The administration of cisplatin can be made by intravenous infusion, intravenous push, bolus injection or subcutaneous injection. In one embodiment, the administration of cisplatin is once every 3 to 4 weeks, while the administration of SNS-595 Substance occurs once per week for three weeks or once every three weeks. In one embodiment, the administration of cisplatin is daily for 5 days, while the administration of SNS-595 Substance occurs once per week for three weeks or once every three weeks. In one embodiment, the administration of cisplatin is once a week for 3 weeks, while the administration of SNS-595 Substance occurs once per week for three weeks or once every three weeks.

In one embodiment, the methods provided include the administration of SNS-595 Substance in combination with about 50 mg/m$^2$ to about 400 mg/m$^2$ carboplatin. For example, one embodiment includes administration of carboplatin at a dose of about 300 or about 360 mg/m$^2$ once every 3 weeks. One embodiment includes administration of carboplatin at a dose of about 300 or 360 mg/m$^2$ once every 4 weeks. The administration of carboplatin can be made by intravenous infusion, intravenous push, bolus injection or subcutaneous injection. In one embodiment, the administration of carboplatin is once every 3 weeks, while the administration of SNS-595 Substance occurs once per week for three weeks or once every three weeks. In one embodiment, the administration of carboplatin is once a week for 3 weeks, while the administration of SNS-595 Substance occurs once per week for three weeks or once every three weeks.

In one embodiment, the methods provided include the administration of SNS-595 Substance in combination with about 100 mg/m$^2$ to about 1500 mg/m$^2$ gemcitabine. For example, one embodiment includes administration of gemcitabine at a dose of about 1000 or 1250 mg/m$^2$ once every week for at least 4 weeks. The administration of gemcitabine can be made by intravenous infusion, intravenous push, bolus injection or subcutaneous injection. In one embodiment, the administration of gemcitabine is once a week for up to 4 weeks, while the administration of SNS-595 Substance occurs once per week for three weeks or once every three weeks. In one embodiment, the administration of gemcitabine is twice a week for 2 weeks, while the administration of SNS-595 Substance occurs once per week for three weeks.

In certain embodiments, the second active agent is co-administered with SNS-595 Substance provided herein or administered with 1-50 hours delay. In certain embodiments, SNS-595 Substance provided herein is administered first followed by administration with the second active agent with 1-50 hours delay. In other embodiments, the second active agent is administered first followed by administration of SNS-595 Substance provided herein with 1-50 hours delay. In some embodiments, the delay is 24 hours.

In another embodiment, the method provided herein comprises: a) administering to a patient in need thereof, a dose of about 10-100 mg/m$^2$ of SNS-595 Substance provided herein and b) administering a therapeutically effective amount of a supportive care agent.

The supportive care agent is any substance that treats, prevents, manages, avoids or reduces an adverse or unwanted effect from treatment with SNS-595 Substance provided herein and is administered according to the appropriate dosing regimen for that substance. For example, different supportive care agents for treating nausea have different dosing regimen. While some such agents are administered prophylactically, others are co-administered with a compound or composition provided herein while still others are administered after the administration of SNS-595. Illustrative examples of supportive care agents their doses and dosing regimens are found in *Physicians' Desk Reference*. Some exemplary support care agents are disclosed in U.S. Application Pub. No. 2006-0025437, which incorporated by reference in its entirety.

4.8 Pharmaceutical Compositions and Dosage Forms

The methods provided herein use pharmaceutical compositions containing SNS-595 Substance provided herein and pharmaceutically acceptable carriers, such as diluents or adjuvants, or in combination with other active ingredient, such as another anti-cancer agent. In certain embodiment, the methods encompass use of pharmaceutical compositions containing substantially pure SNS-595. In clinical practice, SNS-595 Substance may be administered by any conventional route, including but not limited to orally, parenterally, rectally or by inhalation (e.g., in the form of aerosols). Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In one embodiment, SNS-595 Substance is administered by an IV injection.

The pharmaceutical compositions for parenteral administration can be emulsions or homogeneous solutions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, petroleum oil, oil of animal, vegetable or synthetic origin, such as peanut oil, soybean oil, mineral oil, sesame oil and the like. ethyl oleate, isopropyl myristate, and benzyl benzoate.

These pharmaceutical compositions can also contain adjuvants, in particular wetting, isotonizing, emulsifying, dispersing, and stabilizing agents. Sterilization can be carried out in several ways, for example using a 0.2 micron filter, by radiation or by heating (see, *Remington's Pharmaceutical Sciences*, 21st ed., Mack Publishing, Easton, Pa. (2005) (hereinafter "Remington's Pharmaceutical Sciences"). They can also be prepared in the form of sterile solid pharmaceutical compositions which can be dissolved at the time of use in sterile water or any other injectable sterile medium.

Pharmaceutical compositions can be used in the preparation of individual, single unit dosage forms. Pharmaceutical compositions and dosage forms comprise compound and one or more excipients.

Pharmaceutical compositions and dosage forms can also comprise one or more additional active ingredients. Examples of optional second, or additional, active ingredients are disclosed herein.

In certain embodiments, the pharmaceutical composition provided herein is a single unit dosage form. Pharmaceutical compositions and single unit dosage forms provided herein comprise a prophylactically or therapeutically effective amount of compound or composition, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Examples of suitable pharmaceutical carriers are described in *Remington's Pharmaceutical Sciences.*

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The pharmaceutical composition or single unit dosage form, if desired, can also contain minor amounts of wetting or emulsifying agents, or pH buffering agents.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting pharmaceutical composition Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a human or other subject.

A pharmaceutical composition provided herein is formulated to be compatible with its intended route of administration. Examples of routes of administration include, but are not limited to, parenteral routes (i.e., other than through the digestive tract), e.g., intravenous, intradermal, subcutaneous, intramuscular, inhalation, intranasal, transdermal, topical, transmucosal, intra-tumoral, and intra-synovial administration. In a specific embodiment, the composition is formulated in accordance with routine procedures as a pharmaceutical composition adapted for intravenous, subcutaneous, intramuscular, intranasal or topical administration to human beings. In certain embodiments, a pharmaceutical composition is formulated in accordance with routine procedures for subcutaneous administration to human beings. In one embodiment, pharmaceutical compositions for intravenous administration are solutions in sterile isotonic aqueous buffer. Where necessary, the pharmaceutical composition may also include a solubilizing agent and a local anesthetic such as lignocaine to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject. An exemplary solid form is a lyophilized solid.

The pharmaceutical composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington's Pharmaceutical Sciences.*

Generally, the ingredients of pharmaceutical compositions provided herein are supplied either separately or mixed together in unit dosage form, for example, as a dry lyophilized powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients may be mixed prior to administration. In one embodiment, dosage forms provided herein comprise sufficient SNS-595 Substance to permit administration of doses of SNS-595 Substance within the range of about 10-100 mg/m$^2$ per day, or per week, given as a single once-a-day dose or as divided doses throughout the day, optionally taken with food.

In certain embodiments, the pharmaceutical dosage forms provided herein comprise a primary container comprising SNS-595 Substance. In certain embodiments, the primary container is within an opaque secondary container. In one embodiment, the primary container is a glass vial, such as a clear glass vial and the secondary container is an opaque foil-lined pouch, including an opaque metal foil-lined pouch, such as an opaque aluminum foil-lined pouch. In one embodiment, the pharmaceutical dosage forms provided herein comprise a clear glass vial comprising SNS-595 Substance, wherein the clear glass vial is within an opaque aluminum foil-lined pouch. Further, exemplary pharmaceutical dosage forms include those described in WO 2008/016668, incorporated by reference in its entirety. In one embodiment, the dosage forms provided herein comprise about 1-2000, 1-1000, 1-500, 1-300, 1-100 or 1-50 mg of SNS-595 Substance. Particular dosage forms provided herein comprise about 10, 15, 18, 20, 24, 25, 30, 40, 48, 50, 60, 70, 72, 75, 80, 90, 100, 150, 200, 300 or 500 mg of SNS-595 Substance.

5. EXAMPLES

Certain embodiments of the claimed subject matter are illustrated by the following non-limiting examples.

The following abbreviations are used in the examples:
Boc$_2$O=di-tert-butyl-dicarbonate
KHMDS=potassium hexamethyldisilazane
DBDMH=1,3-dibromo-5,5-dimethylhydantoin
TsOH=p-toluene sulfonic acid monohydrate
CDI=carbonyldiimidazole
PGA=pyroglutamic acid
DTTA=di-p-toluoyltartaric acid
CSA=camphor sulfonic acid,
DBTA=dibenzoyltartaric acid,
ACN=acetonitrile,
IPA=isopropyl alcohol,
MeOH=methanol,
THF=tetrahydrofuran and
MTBE=methyl tert-butyl ether.

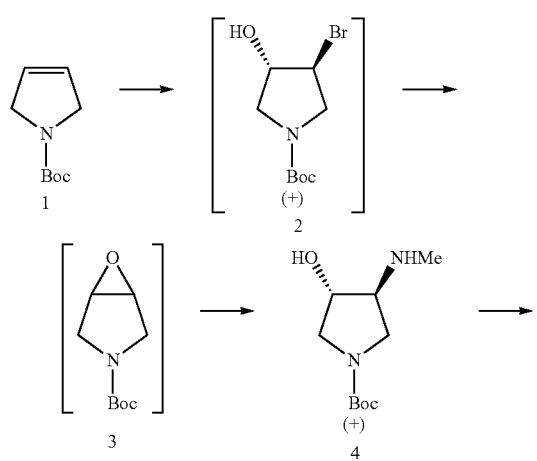

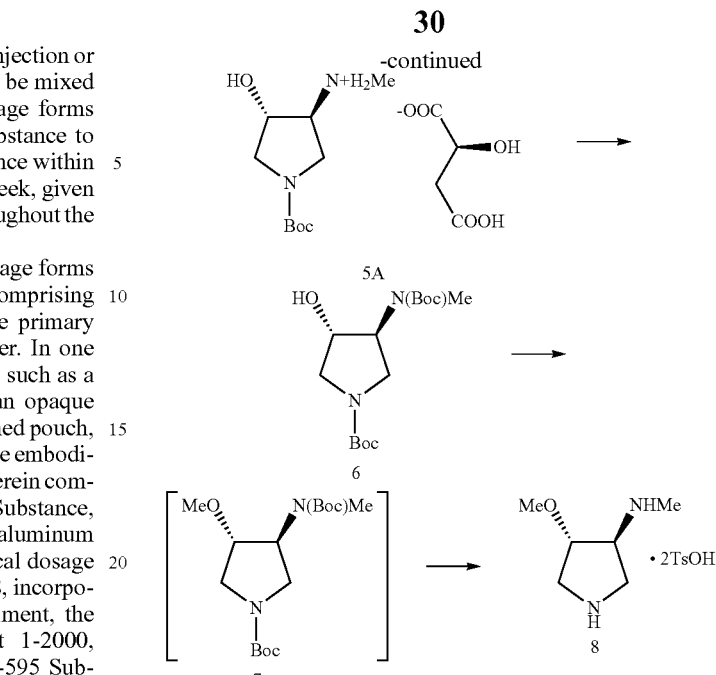

(±)-3-Bromo-4-hydroxy-pyrrolidine-1-carboxylic acid, tert-butyl ester (2). (*Tetrahedron Asymmetry*, 12 (2002) 2989-2997)

N-Boc-3-pyrroline 1 (296 g, 1.75 moles) was added to a slurry of 1,3-dibromo-5,5-dimethylhydantoin (270 g, 0.94 moles) in acetonitrile (ACN, 1800 mL) and water (296 mL), while maintaining the temperature of the vessel at 0 to 10° C. After the addition, the reaction mixture was warmed to room temperature and stirred until the reaction was judged to be complete (TLC or HPLC). The reaction was quenched by the addition of 5% aqueous sodium thiosulfate solution (600 mL) and the product was extracted with dichloromethane (2×750 mL). The combined organic layer was washed with water (300 mL) and brine (200 mL). The organic layer was dried over anhydrous Na$_2$SO$_4$ (75 g) and concentrated under reduced pressure to give 2 (450 g) which was directly used in the next step.

6-Oxa-3-aza-bicyclo[3.1.0]hexane-3-carboxylic acid, tert-butyl ester (3)

An aqueous solution of sodium hydroxide (NaOH, 1.55 L, 2N) was added to compound 2 (450 g, 1.69 moles) and the reaction was stirred between for 2 hr at about room temperature. The product was extracted with dichloromethane (2×1.25 L) and the combined organic layer was washed with water (2×750 mL) to neutral pH and then dried over anhydrous Na$_2$SO$_4$. Evaporation under reduced pressure gave the epoxide 3 (291.0 g).

(±)-3-Hydroxy-4-methylamino-pyrrolidine-1-carboxylic acid, tert-butyl ester (4)

Aqueous methylamine solution (40% solution, 812 mL, 3.8 mol) was added to the epoxide 3 (140 g, 0.65 mol) at room temperature and the reaction was stirred until complete. The excess methylamine was removed by distillation under reduced pressure. To the residue obtained, diisopropyl ether (800 mL) was added and the mixture stirred for about 30 min. The solid was filtered, washed with diisopropyl ether (200 mL), then dried to give compound 4 (135 g).

(±)-3-Hydroxy-4-methylamino-pyrrolidine-1-carboxylic acid, tert-butyl ester (4), from 2

Ten grams (10 g) of bromohydrin 2 was treated with 40% aqueous methylamine (50 mL) and sodium bicarbonate (3.1 g) at room temperature to give Compound 4 (8.5 g).

Resolution of (±)-3-Hydroxy-4-methylamino-pyrrolidine-1-carboxylic acid, tert-butyl ester, Using L-(−)-malic acid The aminoalcohol 4 (100 g, 0.46 moles) was dissolved in a mixture of acetone (600 mL) and water (13 mL) at room temperature. The reaction mixture was heated to about 40° C. and L-(−)-malic acid (62 g, 0.48 moles) was added. The mixture was heated to about 50 to 55° C. to form a clear solution and then gradually cooled to room temperature and then to 5 to 10° C. The crystals formed were filtered, washed with acetone (2×70 mL), and dried under reduced pressure to give the malate salt 5A (60 g, 37%), with purity by chiral HPLC ratio of S to R enantiomers (S:R)=100:0.

A small sample was analyzed for enantiomeric purity by conversion to compound 6 and analyzing the resulting 6 by chiral HPLC (Chiracel OD-H SC\522; mobile phase: hexane: IPA 95:5; 1 mL/min). The retention time for the 5-enantiomer is 7.725 min.

Resolution of (±)-3-Hydroxy-4-methylamino-pyrrolidine-1-carboxylic acid, tert-butyl ester, Using (L)-(−)-pyroglutamic acid Resolution of 4 (10 g) with (L)-(−)-pyroglutamic acid (3.58 g) in acetone (120 mL) and water (4 mL) gave the pyroglutamate salt (5.7 g). Crystallization from acetone-water gave 4.2 g of the PGA salt with 94:6 ratio of diastereomers. An additional recrystallization from acetone-water gave the diastereomerically pure PGA salt (2.3 g, >99% de).

Preparation of 3-(tert-Butoxycarbonyl-methyl-amino)-4-hydroxy-pyrrolidine-1-carboxylic acid, tert-butyl ester (6) from L-(−)-malic acid salt (5A)

To a mixture of compound 5A (57 g, 0.16 moles) in methanol (MeOH, 220 mL), K$_2$CO$_3$ (68.0 g, 0.49 moles) was added at room temperature. Boc anhydride (40 g, 0.18 moles) was added dropwise to the reaction mixture over about 1 hr and the reaction mixture was stirred until the reaction was complete (about 2 hr). Methanol was distilled off under reduced pressure at about 55 to 60° C., water (150 mL) was added to the reaction mixture and the product was extracted with methyl tert-butyl ether (MTBE, 2×150 mL). The combined organic layer was washed with water (200 mL) and brine (100 mL), and then dried over anhydrous Na$_2$SO$_4$. Concentration under reduced pressure gave compound 6 as a white solid (52 g).

3-(tert-Butoxycarbonyl-methyl-amino)-4-methoxy-pyrrolidine-1-carboxylic acid, tert-butyl ester (7)

A suspension of 6 (52 g, 0.16 mol) in tetrahydrofuran (THF, 150 mL) was stirred at room temperature for about 30 min and cooled to −10 to −15° C. A solution of potassium hexamethyldisilylamide (KHMDS, 40% solution in THF, 144 mL, 0.256 mol) was slowly added while controlling the temperature between −5 and −15° C. After 15 min, dimethyl sulfate (18.7 mL, 1.20 mol) was added dropwise to the reaction mixture while maintaining a temperature between −10 and 0° C., and the resulting reaction mixture was then stirred at this temperature for about 30 min. The reaction mixture was quenched by the addition of water (100 mL), followed by acetic acid (50 mL). The product was extracted with methyl tert-butyl ether (2×150 mL). The combined organic layer was washed with water (100 mL), brine (50 mL) and dried over anhydrous Na$_2$SO$_4$. Evaporation under reduced pressure gave compound 7 as an oil (54 g).

(+)-(4-Methoxy-pyrrolidin-3-yl)-methyl-amine, Prepared Using toluene-4-sulfonic acid (2:1)

To a solution of compound 7 (54.0 g, 0.163 moles) in THF (180 mL) and MeOH (90 mL), p-toluene sulfonic acid monohydrate (84 g, 0.442 moles) was added and the reaction mixture was heated to 55 to 60° C. for about 5 hr, at which time the deprotection was complete. After cooling to about 40 to 45° C., 0.2 g seed crystals of 8 was added to the reaction mixture resulting in immediate crystallization. The slurry was maintained at 40 to 45° C. for about 30 minutes and then gradually cooled to 0 to 5° C. After agitating for 2 hr at 0 to 5° C., solids were filtered, washed with THF (2×50 mL), and dried to give the tosylate salt 8 as a white solid (66 g) with HPLC purity=98.9%.

The HPLC conditions were as follows: Column: Chiralcel AD-H, SC\523; mobile phase: Heptane: IPA (0.5% TFA)=85:15; flow rate: 1.0 mL/min, and runtime: 20 min.

Compound 8 has the retention time of 12.66 min. Enantiomeric excess of this material was greater than 99% ee.

Example 2

Resolution of (±)-3-hydroxy-4-methylamino-pyrrolidine-1-carboxylic acid, tert-butyl ester, Using Chiral Acids Resolution of (±)-3-Hydroxy-4-methylamino-pyrrolidine-1-carboxylic acid, tert-butyl ester was attempted by forming salts with various chiral acids. Table 3 provides summary of the reactions. In the table, "Compound 4" refers to (±)-3-hydroxy-4-methylamino-pyrrolidine-1-carboxylic acid, tert-butyl ester. In Table 3, the enantiomeric ratio by chiral HPLC is represented as S:R. In experiment nos. 72, 74 and 75 onwards, HPLC analysis was performed at compound 6 stage.

TABLE 3

Study of resolution with various resolving agents:

| | Cmpd 4 Input (g)/Eq | Chiral acid (g)/Eq | Reaction temp. (° C.) | Reaction time (hr) | Procedure/results |
|---|---|---|---|---|---|
| | | | Resolution using L-(+)-Tartaric acid | | |
| 1 | 0.5 g | 0.174 g | 25-30 | | Compound 4:L-(+)-Tartaric Acid were used in 2:1 ratio. Crystallization was done in isopropyl alcohol (IPA). Specific Optical Rotation (SOR) of the tartrate complex = +11.024. |
| 2 | 1.0 g | 0.3472 g | 25-30 | 4 | Compound 4:L-(+)-Tartaric Acid were used in 2:1 ratio. Crystallization was done in IPA. Yield = 0.4 g, 40.0%; SOR of the tartrate complex = +12.8. The complex was broken to give free amine, which gave SOR of +1.5 & Chiral HPLC ratio = 48.73:44.57 (S:R). |
| 3 | 1.0 g | 0.1736 g | 55-60 | 1 | Compound 4 and L-(+)-Tartaric Acid were used in 1:0.25 ratio. Glacial acetic acid was used as solvent. No crystal formation observed. |
| 4 | 1.0 g | 0.1736 g | 55-60 | 1 | Compound 4 and L-(+)-Tartaric Acid were used in 1:0.25 ratio. Dry MeOH was used for complex formation, & crystallization was carried out in IPA. White solid (428.0 mg) with SOR = +12.754. |
| 5 | 1.0 g | 0.520 g | 55-60 | 1 | Compound 4 and L-(+)-Tartaric Acid were used in 1.0:0.75 ratio. MeOH was used for complex formation, & crystallization attempted in MeOH:IPA mixture (2:4 mL), MeOH:water mixture (4:1 mL), acetone:water (8:2 mL). None of these methods gave crystals. |
| 6 | 1.0 g | 0.6944 g | 55-60 | 1 | Compound 4 and L-(+)-Tartaric Acid were used in 1:1 ratio. No crystal formation. |
| 7 | 0.5 g | L-(+)-Tartaric acid 0.174 g; AcOH 0.069 g | 60-65 | 30.0 min | A family of resolving agents was used. Stoichiometry of Compound 4:L-(+)-Tartaric Acid:Acetic Acid = 1:0.5:0.5. Crystallization was done in EtOH + MIBK + acetone (2:10:5 mL). Complex = 0.34 g. (SOR = +11.8) & complex was broken, which was 51.82:48.17 enantiomeric ratio (S:R) by chiral HPLC. |
| 8 | 0.5 g | 0.347 g | 55-60 | 30.0 min | Compound 4 and L-(+)-Tartaric Acid were used in 1:1 ratio. Complex formation was attempted with $CuSO_4$ in MeOH & crystallization was attempted in NaOH soln. No crystal formation. |
| | | | Resolution using D-(−)-Tartaric acid | | |
| 9 | 1.0 g | 0.347 g | 25-30 | 4 | Compound 4 and D-(−)-Tartaric Acid were used in 1:0.5 ratio. MeOH was used for complex formation, and IPA for crystallization. Isolated complex, 850.0 mg SOR = −11.598. Recrystallization was attempted in ACN + $H_2O$, acetone + $H_2O$, ACN + MeOH. No crystal formation. 400.0 mg of crude complex (SOR = −11.598) after crystallization from ACN:IPA mixture gave 130.0 mg of crystals with SOR = −10.59 |
| 10 | 1.0 g | 0.1735 g | 25-30 | 4 | Compound 4 and D-(−)-Tartaric Acid were used in 1:0.25 ratio. MeOH was used for complex formation, and IPA for crystallization. Isolated complex = 420 mg. Recrystallization in IPA gave 180.0 mg of complex with SOR= −12.351. Breaking this complex gave 120.0 mg of solid with SOR = +0.218. |
| | | | Resolution using (+)-Mandelic acid | | |
| 11 | 0.5 g | 0.350 g | 60-65 | 2 | Compound 4:(+)-Mandelic acid were used in 1:1 ratio. Complex formation was attempted in MeOH, & crystallization attempted in MeOH, IPA, and $CH_3CN$. No crystal formation. |
| 12 | 0.5 g | 0.264 g | 55-60 | 30.0 min | Stoichiometry of Compound 4:(+)-Mandelic Acid = 1:0.75. Complex formation was done in MeOH, & crystallization was done in MIBK. Crystal formation was not observed. |
| | | | Resolution using (+)-DTTA | | |
| 13 | 1.0 g | 0.4472 g | 55-60 | 1 | Compound 4:(+)-DTTA = 1:0.25. EtOH used for complex formation, & IPA for crystallization. Crystallization in EtOH, EtOH:IPA mixture did not produce crystals. |
| 14 | 0.5 g | 0.8944 g | 55-60 | 1 | Compound 4:(+)-DTTA = 1:1. Isolated complex = 0.665 g Crystallized from THF:MTBE = 3.0 mL:12 mL. Yield = 0.03586 g; SOR (complex) = +86.40. Enantiomeric ratio (S:R) = 46.107:49.715. |
| 15 | 0.5 g | 0.4472 g | 55-60 | 1 | Compound 4: (+)-DTTA = 1: 0.5. Complex formation in MeOH and crystallization in acetone, IPA, EtOH + MTBE, THF, THF + MTBE mixture. No crystal formation. |
| 16 | 0.5 g | 0.67 g | 55-60 | 1 | Stoichiometry of Compound 4:(+)-DTTA = 1:0.75. Complex formation was performed in THF, and crystallization with THF:MTBE = 1:4 gave sticky solid with SOR = +70.057. |
| | | | Resolution using S-(+)-CSA and R-(−)-CSA | | |
| 17 | 0.5 g | S-(+)-CSA, 0.5377 g | 55-60 | 2 | Compound 4:S-(+)-CSA =1:1. Complex formation in acetone and crystallization in various solvents incl. acetone, EtOH + MTBE, acetone + MTBE, ACN. No crystal formation. Sticky mass. |

TABLE 3-continued

Study of resolution with various resolving agents:

| | Cmpd 4 Input (g)/Eq | Chiral acid (g)/Eq | Reaction temp. (° C.) | Reaction time (hr) | Procedure/results |
|---|---|---|---|---|---|
| 18 | 0.2 g | S-(+)-CSA, 0.1075 g | 55-60 | 1 | Compound 4:S-(+)-CSA = 1:0.5. Complex formation in MeOH and crystallization in different solvent system did not produce any crystals/solid. |
| 19 | 0.2 g | S-(+)-CSA 0.1613 g | 55-60 | 1 | Compound 4:S-(+)-CSA = 1:0.75. Complex formation was performed in MeOH. Crystallization did not give any crystals/solid. |
| 20 | 0.5 g | R-(−)-CSA 0.1613 g | 55-60 | 15 min | Compound 4:R-(−)-CSA = 1:0.5. Complex formation in acetone. No crystal formation. |
| | | | | | Resolution using Pyroglutamic Acid and Dibenzoyltartaric acid (DBTA) |
| 21 | 0.5 g | (+)-DBTA 0.6539 g | 55-60 | 30.0 min | Stoichiometry of Compound 4:(+)-DBTA = 1:0.75. Complex formation was performed in THF and crystallization was attempted in various solvents incl. acetone, IPA, EtOH + MTBE, THF, THF + MTBE mixture. Crystal formation not observed. |
| 22 | 0.5 g | (+)-DTTA 0.445 g; (+)-DBTA 0.435 g | 55-60 | 30.0 min | Family of resolving agents was used. Stoichiometry of Compound 4:DTTA:DBTA = 1:0.5:0.5. Crystallization was done in ACN + MTBE (2:12 mL). Yield = 0.5 g with SOR = +78.126. |
| 23 | 0.5 g | L-(−)-PGA 0.298 g | 55-60 | 30.0 min | Stoichiometry of Compound 4:L-(−)-PGA = 1:1. Complex formation & crystallization was done in acetone. White solid crystallized out = 0. 22 g with SOR = +4.377. Complex was broken to give isomer with SOR = −1.12. HPLC enantiomer ratio (S:R) = 84.037:15.963. |
| 24 | 0.5 g | L-(−)-PGA 0.224 g | 55-60 | 30.0 min | Stoichiometry Compound 4:L-(−)-PGA = 1:0.75. Complex formation & crystallization was done in acetone. White solid crystallized out = 0. 200 g with SOR = +3.613. Complex was broken to give isomer with SOR = −1.175. HPLC enantiomeric ratio (S:R) = 81.15:16.34. |
| 25 | 0.5 g | L-(−)-PGA 0.149 g | 55-60 | 30.0 min | Stoichiometry of Compound 4:L-(−)-PGA = 1:0.5. Complex formation & crystallization was done in acetone. Yield (Complex) = 0.200 g ; SOR = +5.560. Broken isomer SOR = −0.856. |
| 26 | 1.0 g | L-(−)-PGA 0.597 g | 55-60 | 30.0 min | Stoichiometry of Compound 4: L-(−)-PGA = 1:1. Complex formation was done in acetone + MeOH (10 mL + 5 mL) & crystallization in acetone. Complex = 0. 600 g; SOR = +3.675. Complex was broken to give enantiomer with SOR = +0.210; enantiomers ratio by chiral HPLC as 75:25 (S:R). |
| 27 | 1.0 g | L-(−)-PGA 0.597 g | 55-60 | 30.0 min | Stoichiometry of Compound 4:L-(−)-PGA = 1:1. Complex formation was done in ACN + H$_2$O & crystallization in ACN. Complex = 0.460 g ; SOR = +5.560. Complex was broken to give isomer with SOR = −1.191. HPLC enantiomers = 77.202:22.798 (S:R). |
| 28 | 0.5 g | L-(−)-PGA, 0.299 g | 80-90 | 30.0 min | Stoichiometry of Compound 4:L-(−)-PGA = 1:1. Complex formation was done in t-BuOH. No crystal formation. |
| 29 | 1.0 g | L-(−)-PGA, 0.597 g | 80-90 | 30.0 min | Stoichiometry of Compound 4:L-(−)-PGA = 1:1. Complex formation in n-Pentanol gave 0.6 g with SOR = 2.98; Complex was broken to give 0.45 g of enantiomer, SOR = −1.93 and enantiomeric ratio by HPLC = 70.795:29.20 (S:R). |
| 30 | 3.0 g | L-(−)-PGA 1.79 g | 55-60 | 30.0 min | Stoichiometry of Compound 4:L-(−)-PGA = 1:1. Recrystallization was done in acetone: MeOH mixture. Three crops were obtained. 1st crop 920.0 mg with enantiomeric ratio 78.8:20.96 (S:R) and SOR = −0.297; 2nd crop = 1100 mg with enantiomeric ratio 95.49:4.5 (S:R) and SOR = −1.874; 3rd crop = 700 mg with enantiomeric ratio 0:100 (S:R) and SOR = +0.900. |
| 31 | 1.0 g | L-(−)-PGA 0.597 g | 55-60 | 30 min | Stoichiometry of Compound 4:L-(−)-PGA = 1:1. Recrystallization was done in THF. Complex (0.5 g) was broken to give enantiomer with HPLC ratio 63.2:36.8 (S:R) & SOR = +0.218. |
| 32 | 1.0 g | L-(−)-PGA 0.597 g | 55-60 | 1.0 | Stoichiometry of Compound 4:L-(−)-PGA = 1:1. Recrystallization in IPA:MIBK (10:5 mL) gave 0.4 g complex. The complex was broken to give enantiomer with HPLC ratio 74.71:25.29 (S:R) and SOR = −0.307. |
| 33 | 0.5 g | L-(−)-PGA 0.2986 g | 55-60 | 1.0 | Stoichiometry of Compound 4:L-(−)-PGA = 1:1. Recrystallization in IPA:MEK (4:8 mL) gave 0.26 g complex. Complex was broken to give enantiomer with HPLC ratio 80.71:19.28 (S:R); SOR = −2.198. |
| 34 | 0.5 g | L (−)-PGA 0.1495 g; L-Proline, 0.13g | 60-65 | 1.0 | Compound 4:L-(−)-PGA:L-Proline = 1:0.5:0.5. Recrystallization was attempted in MeOH, but no crystal formation was observed. |
| 35 | 1.0 g | L (−)-PGA 0.298 g; Propionic Acid, 0.171 g | 40-45 | 1.0 | Compound 4:L-(−)-PGA:Propionic Acid = 1:0.5:0.5. Complex formation & crystallization was done in acetone. Complex = 0.43 g and complex was treated with aq. K$_2$CO$_3$ to give enantiomer (0.258 g) with SOR = −1.274. HPLC ratio 81.36:18.63 (S:R). |
| 36 | 1.0 g | L-(−)-PGA 0.298 g; | 40-45 | 1.0 | Stoichiometry of Compound 4:L-(−)-PGA:Propionic Acid = 1:0.5:0.5. Complex formation & crystallization was done in |

TABLE 3-continued

Study of resolution with various resolving agents:

| | Cmpd 4 Input (g)/Eq | Chiral acid (g)/Eq | Reaction temp. (° C.) | Reaction time (hr) | Procedure/results |
|---|---|---|---|---|---|
| | | Propionic Acid 0.171 g | | | acetone. White solid ppt out = 0.401 g and complex was broken using $K_2CO_3$ to give isomer (0.238 g) with SOR = +0.098. HPLC ratio 82.16:17.84 (S:R). |
| 37 | 1.0 g | L-(−)-PGA 0.2986 g | 85-90 | 1.0 | n-Pentanol used as solvent for complex formation and recrystallization. Compound 4:L-(−)-PGA = 1:0.5. Crystallization was achieved with mixture of n-Pentanol and MIBK. Pentanol alone doesn't yield any crystallization. SOR = +1.022. HPLC ratio 75.36: 24.63 (S:R). |
| 38 | 1.0 g | L-(−)-PGA 0.2986 g | 85-90 | 1.0 | 2-Propanol used as solvent for complex formation and recrystallization. No crystal formation observed. |
| 39 | 1.0 g | L-(−)-PGA 0.358 g | 40-50 | 1.0 | Stoichiometry of Compound 4:L-(−)-PGA = 1:0.6. Acetone:water (12:0.4 mL) mixture was used for complex formation and recrystallization with acetone:water (10:0.4 mL). SOR of the enantiomer = −0.89. Purity by HPLC = 98.70%. |
| 40 | 10.0 g | L-(−)-PGA 5.37 g | 85-90 | 1.0 | Stoichiometry of Compound 4:L-(−)-PGA = 1:0.9. Methyl ethyl ketone:IPA (100:40 mL) mixture used for complex formation (6.7 g) and IPA:MEK (30:45 mL) mixture used for recrystallization: complex = 4.3 g, Chiral HPLC S:R = 91.74:8.26. The complex was 2nd recrystallized gave 3.0 g of the complex. Chiral HPLC S:R = 95.4:4.6. |
| 41 | 10.0 g | L-(−)-PGA 3.58 g | 40-50 | 1.0 | Stoichiometry of Compound 4:L-(−)-PGA = 1:0.6. Acetone:water (120:4 mL) mixture was used for complex formation and crystallization (5.7 g). Recrystallization with acetone:water gave 4.2 g (Chiral HPLC S:R = 93.6:6.4). $2^{nd}$ time recrystallization with acetone:water mixture gave 2.3 g of complex (Chiral HPLC S:R = 100:0). |
| 42 | 1.0 g | L-(−)-PGA 0.2986 g | 85-90 | 1.0 | n-Pentanol:Acetone (15:5 mL) mixture was used for complex formation. Stoichiometry of Compound 4:L-(−)-PGA = 1:0.5. No crystallization. |
| 43 | 1.0 g | L-(−)-PGA 0.2986 g | 50-55 | 1.0 | Compound 4:L-(−)-PGA = 1:0.5. IPA:acetone (2:13 mL) mixture was used for complex formation (0.411 g) by stirring at RT for 2 h and cooled to 0-10 ° C. and the complex was broken to give enantiomer (0.1886 g, Chiral HPLC S:R = 79:18) with SOR = −1.0. |
| 44 | 1.0 g | L-(−)-PGA 0.597 g | 50-55 | 1.0 | Compound 4:L-(−)-PGA = 1:1. IPA:acetone (2:13 mL) mixture was used for complex formation (0.7496 g) and the complex (SOR = 3.968) was broken to give enantiomer (0.386 g) with SOR = −0.959, Chiral HPLC S:R = 80.58:19.29. |
| 45 | 1.0 g | L-(−)-PGA 0.2986 g | 50-55 | 1.0 | Compound 4:L-(−)-PGA = 1:1. IPA:Acetone (2:13 mL) mixture was used for complex formation (0.471 g) by stirring at RT overnight and cooled to 0-10 ° C. and the complex was broken to give enantiomer (0.2711 g, Chiral HPLC S:R = 89.98:10.02) with SOR = −0.689. |
| 46 | 10.0 g | L-(−)-PGA 5.98 g | 40-50 | 1.0 | Compound 4:L-(−)-PGA = 1: 1. Acetone:MeOH (130:10 mL) mix was used for complex formation and crystallization gave 7.6 g (Chiral HPLC S:R = 83.3:16.7). Recrystallized with acetone:MeOH:water mix gave 3.9 g (Chiral HPLC S:R = 88.69:11.3). |
| 47 | 10.0 g | L-(−)-PGA 3.0 g | 40-50 | 1.0 | Compound 4:L-(−)-PGA = 1:0.5. Acetone:water (80:2.5 mL) mix used for complex formation & crystallization gave 4.8 g (S:R = 78.23:21.77). Then it was recrystallized with acetone:water mixture gave 3.4 g Chiral HPLC S:R = 86.98:13.02. |
| 48 | 10.0 g | L-(−)-PGA 3.5 g | 40-50 | 1.0 | Stoichiometry of Compound 4:L-(−)-PGA = 1:0.59. Acetone:MeOH (80:5 mL) mixture was used for complex formation and crystallization gave 6.0 g Chiral HPLC S:R = 79.78:20.21. |
| 49 | 10.0 g | L-(−)-PGA 5.97 g | 50-60 | 1.0 | Compound 4:L-(−)-PGA = 1:1. IPA used for complex formation and (IPA:acetone = 1:5) mix for crystallization (11.0 g). Broken complex (3.71 g); enantiomer (S:R = 68.2:31.7). |
| 50 | 20.0 g | L-(−)-PGA 11.94 g | 50-60 | 1.0 | Compound 4:L-(−)-PGA =1:1. Acetone used for complex formation and crystallization (15.1 g) and the complex was broken to give the 8.65 g of enantiomer. Chiral enantiomeric S:R = 76.77:23.23. MLR was concentrated, Wt = 9.0 g, Chiral HPLC Compound 6 S:R = 26.84:73.16. |
| 51 | 2.0 g | L-(−)-PGA 0.6069 g | 50-60 | 1.0 | Compound 4:L-(−)-PGA:Conc. HCl = 1:0.5:0.5. Acetone (20 mL) was used for complex formation and crystallization (44.0 mg). |
| 52 | 2.0 g | L-(−)-PGA 0.717 g | 50-60 | 1.0 | This is a second resolution of enantiomer (S:R = 71.0:29.0) obtained in Experiment 70 below. Compound 4:L-(−)-PGA = 1:0.6. Acetone:water (24:0.8 mL) was used for complex formation and crystallization (2.56 g). The complex was broken to give 1.7 g of enantiomer. Analysis by chiral HPLC (S:R = 96.5 : 3.2). |
| | | | | | Resolution using Proline and Lactic Acid |
| 53 | 0.5 g | L-Proline 0.2665 g | 60-65 | 1.0 | Compound 4:L-Proline = 1: 1. Recrystallization in MeOH gave 0.07 g of complex with SOR = −86.046. |

TABLE 3-continued

Study of resolution with various resolving agents:

| | Cmpd 4 Input (g)/Eq | Chiral acid (g)/Eq | Reaction temp. (° C.) | Reaction time (hr) | Procedure/results |
|---|---|---|---|---|---|
| 54 | 2.0 g | L-Proline 1.066 g | 60-65 | 1.0 | Compound 4:L-Proline = 1: 1. Recrystallization in MeOH gave 0.98 g; SOR = −84.93. |
| 55 | 0.5 g | Boc-L-Proline 0.5 g | 45-50 | 1.0/O.N | Compound 4:Boc-L-Proline = 1:1. Acetone was used for complex formation and crystallization. Crystallization not observed. |
| 56 | 0.5 g | Boc-L-Proline 0.5 g | 55-60 | 1.0 RT-O.N | Compound 4:Boc-L-Proline = 1:1. MeOH used for complex formation and crystallization. Crystallization not observed. |
| 57 | 0.5 g | Boc-L-Proline 0.5 g | 75-80 | 1.0 RT-O.N | Compound 4:Boc-L-Proline = 1:1. IPA used for complex formation and crystallization. Crystallization not observed. |
| 58 | 0.5 g, | L(+)-Lactic Acid 0.2 g | 50-55 | 1 | Compound 4:L-Lactic Acid = 1:1. Various solvents incl. acetone, MeOH, MDC and IPA attempted. Crystallization not observed. |
| Resolution using Malic acid | | | | | |
| 59 | 0.5 g | D-(+)-Malic Acid 0.3103 g | 50-55 | 1.0 | Compound 4:D-(+)-Malic Acid = 1:1. Complex (0.58 g) formation done in acetone (10.0 mL) and Isomer = 0.335 g with SOR = +0.851 and chiral HPLC ratio of S:R = 16.56:83.4. |
| 60 | 1.0 g | D-(+)-Malic Acid 0.155 g | 50-55 | 1.0 | Compound 4:D-(+)-Malic Acid = 1:0.25. Acetone:water (12:0.4) mix for complex formation and crystallization gave 0.54 g and recrystallization with acetone:water gave 0.24 g with chiral HPLC S:R = 54.74:45.26. |
| 61 | 1.0 g | D-(+)-Malic Acid 0.31 g | 50-55 | 1.0 | Stoichiometry of Compound 4:D-(+)-Malic Acid = 1:0.5. Acetone:IPA mixture used for complex formation and crystallization gave 0.75 g and chiral HPLC S:R = 53.0:47.0). |
| 62 | 0.5 g | D-(+)-Malic Acid 0.774 g | 45-50 | 1.0 | Compound 4:D-(+)-Malic Acid = 1:0.25. Acetone used for complex formation and crystallization gave 0.231 g and the complex was broken with aq. $K_2CO_3$ to give 0.1886 g of enantiomer with SOR = +1.637 and chiral HPLC S:R = 51.66:48.3). |
| 63 | 0.5 g | D-(+)-Malic Acid 0.155 g | 45-50 | 1.0 | Compound 4: D-(+)-Malic Acid = 1:0.5. Acetone used for complex formation and crystallization gave 0.5365 g, and the complex was broken with aq. $K_2CO_3$ to give 0.2986 g of enantiomer with SOR = −2.231; chiral HPLC S:R = 45.93:54.07. |
| 64 | 1.0 g | D-(+)-Malic Acid 0.155 g | 45-50 | 1.0 | Compound 4:D-(+)-Malic Acid =1:0.25. IPA used for complex formation and crystallization gave 0.450 g and 50.0 mg of the complex was broken with aq.$K_2CO_3$ to give enantiomer with chiral HPLC S:R = 52.49:47.5. |
| 65 | 0.5 g | L-(−)-Malic Acid 0.31 g | 50-55 | 1 h | Compound 4:L-(−)-Malic Acid =1:1. Acetone was used. Complex = 0.312 g & complex was broken with aq. $K_2CO_3$ to give enantiomer (0.1825 g). Chiral HPLC S:R = 83.6:13.7. |
| 66 | 5.0 g | L-(−)-Malic Acid 3.103 g | 50-55 | 1 | Compound 4:L-(−)-Malic Acid = 1:1. Acetone was used. Complex = 3.51 g and the complex was broken with aq. $K_2CO_3$ to give enantiomer (1.725 g). Chiral HPLC S:R = 81.3:18.7 |
| 67 | 2.0 g | L-(−)-Malic Acid 1.24 g | 60-70 | 1.0 | Compound 4:L-(−)-Malic Acid = 1:1. IPA was used for complex formation and crystallization. Crystallization not observed. |
| 68 | 2.0 g | L-(−)-Malic Acid 1.24 g | 50-60 | 1.0 | Compound 4:L-(−)-Malic Acid = 1:1. IPA used for complex formation & IPA:acetone mix used for crystallization (1.188 g). Complex was broken, gave 0.5639 g of enantiomer. Chiral HPLC = 100.00%. |
| 69 | Complex 2.0 g (S:R = 76.77:23.2) | L (−)-Malic Acid 1.24 g | 50-60 | 1.0 | This is a second resolution of enantiomer (S:R = 26.84:73.16) obtained in Experiment 50 above. 2.0 g of malic acid complex (S:R = 76.77:23.2) was taken for further resolution with L-(−)-malic acid. Stoichiometry of Compound 4:L-(−)-Malic Acid = 1:1. 10 V (20.0 mL) of acetone:IPA mix used for complex formation and crystallization (1.6 g). Enantiomer (1.15 g, S:R = 99.4:0.3) was obtained after breaking the complex. |
| 70 | 20.0 g | L-(−)-Malic Acid 11.95 g | 50-60 | 1.0 | Compound 4:L-(−)-Malic Acid = 1:1. 4 V (80.0 mL) of acetone:IPA mix used for complex formation and crystallization (15.5 g) and the complex was broken to give 8.60 g of enantiomer. Chiral HPLC S:R = 71.0:29.0. |
| 71 | 3.3 g | D-(+)-Malic Acid 2.0 g | 50-60 | 1.0 | This is a second resolution of enantiomer (S:R = 26.84:73.16) obtained in Experiment 50 above. Compound 4:D-(+)-Malic Acid = 1:1. Acetone (50.0 mL) used for complex formation & crystallization (3.5 g). Complex was broken to give 2.0 g of enantiomer. Chiral HPLC S:R = 0.81:99.19. |
| 72 | 3.0 g | L-(−)-Malic Acid 1.86 g | 50-60 | 1.0 | Compound 4:L-(−)-Malic Acid = 1:1. Acetone:water (30:1 mL) was used for complex formation and crystallization (1.6 g). Chiral HPLC (Compound 6) S:R = 97.0:3.0. |
| 73 | 10.0 g | L-(−)-Malic Acid 6.2 g | 50-60 | 1.0 | Compound 4:L-(−)-Malic Acid = 1:1. Acetone:water (70:2 mL) mix was used for complex formation and crystallization (5.6 g). Chiral HPLC analysis Compound 6 (S:R = 100:0). MLR was concentrated, Wt = 10.5 g Chiral HPLC S:R = 18.2:81.8). |
| 74 | 10.0 g | L-(−)-Malic Acid 6.2 g | 50-60 | 1.0 | Compound 4:L-(−)-Malic Acid = 1:1. Acetone:water (60:2 mL) mix was used for complex formation and crystallization (5.5 g). Chiral HPLC Compound 6 S:R = 100:0. |

TABLE 3-continued

Study of resolution with various resolving agents:

| Cmpd 4 Input (g)/Eq | Chiral acid (g)/Eq | Reaction temp. (° C.) | Reaction time (hr) | Procedure/results |
|---|---|---|---|---|
| 75 1.47 g | L-(−)-PGA 0.44 g; L-(−)-Malic Acid, 0.45 g | 50-55 | 1.0 | Compound 4:L-(−)-PGA:L-(−)-Malic Acid = 1:0.5:0.5. Acetone (10.0 mL) was used as solvent. Complex = 300 mg. Chiral HPLC Compound 6 S:R = 87.17:12.83. |
| 76 1.0 g | L-(−)-Malic acid 0.31 g; AcOH, 0.14 g | 40-45 | 1.0 | Compound 4:L-(−)-Malic Acid:Acetic Acid = 1:0.5:0.5. Complex formation & crystallization was done in acetone (7.0 mL). Solid ppt out = 0.35 g. Chiral HPLC S:R = 100.0:0.0. |
| 77 5.0 g | L-(−)-Malic Acid 3.10 g | 50-55 | 1 | Stoichiometry of Compound 4:L-(−)-Malic Acid = 1:1. Acetone:water (30:0.5 mL) was used. Minimum amt of water used to check the change in yield and purity. Filtration of crystals at 20-25° C. Complex = 3.1 g. Chiral HPLC S:R = 100.0:0.0. |
| 78 5.0 g | L-(−)-Malic Acid 3.10 g | 50-55 | 1 | Compound 4:L-(−)-Malic Acid = 1:1. Acetone:water (30:0.5 mL). Minimum amt water used to check change in yield & purity. Filtration at 0-5° C. Complex = 3.2 g Chiral HPLC S:R = 99.20:0.80. |
| 79 2.0 g | L-(−)-Malic Acid 1.2416 g | 50-55 | 1 | Compound 4:L-(−)-Malic Acid = 1:1. Acetone:MeOH (10:3 mL) was used as solvent. Complex = 0.90 g. Chiral HPLC S:R = 100.0:0. |
| 80 3.0 g | L-(−)-Malic acid 1.864 g | 50-55 | 1 | Compound 4:L-(−)-Malic Acid = 1:1. Acetone:MeOH (10:3 mL) was used. Complex = 1.1437 g. |
| 81 100 g | L-(−)-Malic acid 62.0 g | 50-55 | 1 | Compound 4: L-(−)-Malic Acid = 1:1. Acetone:water (600:18 mL) used. Complex = 57.0 g. Chiral HPLC S:R = 100.0:0. |
| 82 1.04 g | L-(−)-Malic acid 0.64 g | 50-55 | 1 | Crude Compound 4 was used. Stoichiometry of Compound 4:L-(−)-Malic Acid = 1:1. Acetone:water (6:0.1 mL) mix was used. Complex = 0.5 g. Chiral HPLC S:R = 99.2:0.8. |
| 83 1.8 g | L-(−)-Malic acid 1.1 g | 50-55 | 1 | Compound 4:L-(−)-Malic Acid = 1:1. Acetone:water (12:0.2 mL) used. Complex = 1.0 g. Chiral HPLC S:R = 100.0:0.0. Note: Crude epoxide & crude Compound 4 were used. |
| 84 1.2 g | L-(−)-Malic acid 0.73 g | 50-55 | 1 | Compound 4:L-(−)-Malic Acid = 1:1. Acetone:water (10:0.2 mL) used. Complex = 0.82 g. Chiral HPLC S:R = 100.0:0.0. Note: Crude epoxide & crystallized Compound 4 were used. |
| 85 100 g | L-(−)-Malic acid 62.0 g | 50-55 | 1 | Compound 4:L-(−)-Malic Acid = 1:1. Acetone:water (600:13 mL) used. Complex = 60.0 g. Chiral HPLC S:R = 100.0:0. Min. amt of water used for crystallization. |
| 86 2.0 g | L-(−)-Malic acid 1.2 g | 50-55 | 1 | Crude Compound 4 obtained from direct synthesis through bromohydrin was used. Stoichiometry of Compound 4:L-(−)-Malic Acid = 1:1. Acetone:water (15:0.2 mL) mix was used. No crystallization observed. |
| 87 8.0 g 80.0% purity | L-(−)-Malic Acid 4.0 g | 50-55 | 1 | Compound 4:L-(−)-Malic Acid = 1:1. Acetone:water (40:0.5 mL) was used. Complex = 3.6 g. Chiral HPLC S:R = 98.04:1.96. Compound 4 directly prepared from bromohydrin was used. Malic acid quantity used was based on purity of the crude Compound 4. |
| 88 58.0 g 84.3% purity | L-(−)-Malic Acid 36.0 g | 50-55 | 1 | Compound 4:L-(−)-Malic Acid = 1:1. Acetone:water (360:5 mL) was used. Complex = 32.0 g. Chiral HPLC S:R = 99.4:0.6. Compound 4 directly prepared from crude epoxide was used. |
| 89 40.0 g 79% purity | L-(−)-Malic Acid 24.8 g | 50-55 | 1 | Compound 4:L-(−)-Malic Acid = 1:1. Acetone:water (240:4 mL) was used. Complex = 20.0 g. Chiral HPLC S:R = 94.9:5.1. Compound 4 directly prepared from bromohydrin was used. Malic acid quantity was used based on weight of the crude Compound 4. |
| 90 53.0 g | L-(−)-Malic Acid 32.8 g | 50-55 | 1 | Compound 4:L-(−)-Malic Acid = 1:1. Acetone:water (300:5 mL) was used. Complex = 30.2 g. Chiral HPLC S:R = 95.1:4.9. Malic acid quantity was used based on weight of the crude Compound 4. Moisture content by Kf = 1.7% |
| 91 10.0 g | L-(−)-Malic Acid 6.2 g | 50-55 | 1 | Compound 4:L-(−)-Malic Acid = 1:1. Acetone:water (60:1 mL) was used. Complex = 9.0 g. Chiral HPLC S:R = 65.6:34.4. Aqueous Compound 4 solution (40%, 0.25 mL) was deliberately added to the reaction mass to understand the effect of free Compound 4. Yellow sticky mass (complex). NMR showed impurity peak. |
| 92 5.0 g | L-(−)-Malic Acid 3.1 g | 50-55 | 1 | Compound 4:L-(−)-Malic Acid = 1:1. Acetone:water (30:0.6 mL) was used. Complex = 4.0 g. Chiral HPLC S:R = 70.7:29.3. 0.5% Free Compound 4 (0.06 mL 40% aq. soln) was added to the reaction mass. Complex becomes slightly sticky (yellow). |
| 93 10.0 g | L-(−)-Malic Acid 6.2 g | 50-55 | 1 | Compound 4:L-(−)-Malic Acid = 1:1. Acetone:water (60:1 mL) was used. Complex = 5.8 g. Chiral HPLC S:R = 98.6:1.4. Free Compound 4 was not added to the reaction mass. Complex obtained as white, free flowing solid. |

As seen from the data, resolution of (±)-3-hydroxy-4-methylamino-pyrrolidine-1-carboxylic acid, tert-butyl ester with L-(−)-malic acid (1:1) produces S enantiomer in up to 100% enantiomeric excess.

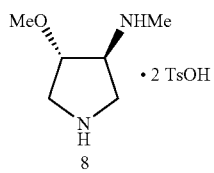

N-Boc-3-pyrroline (1) (16 kg) was treated with 1,3-dibromo-5,5-dimethylhydantoin (DBDMH) (15.2 kg) in aqueous ACN to form the bromohydrin (2). After the reaction was complete, the excess brominating agent was quenched with aqueous sodium thiosulfate solution and the crude reaction mixture was treated with aqueous NaOH. The resulting epoxide was extracted with MTBE and the organic layer was concentrated to give the crude epoxide (3). This epoxide was added to 40% aqueous methylamine and, after the reaction was complete, the excess methylamine and water were removed by distillation and the product, (4), (18.5 kg) was isolated from diisopropyl ether.

Racemic compound 4 (18.4 kg) was resolved by treatment with L-(−)-malic acid (11.4 kg) in aqueous acetone. The (S,S)-isomer (5) crystallized as the L-(−)-malate salt (5A). This was filtered and the filter cake was washed with acetone and dried to give compound 5A (11.8 kg).

A slurry of compound 5A (11.8 kg) and potassium carbonate (11.7 kg) in methanol was treated with Boc-anhydride (Boc$_2$O) (8.3 kg) until the reaction was complete. The product was extracted with MTBE. The organic layer was dried by distillation and petroleum ether added. The slurry was filtered, washed with petroleum ether and dried to give compound 6 (9.9 kg).

Compound 6 (9.9 kg) was treated with a solution of KHMDS (35 kg, 20% w/w) in THF, followed by dimethyl sulfate (4.7 kg). After completion of the reaction, the reaction mixture was quenched with 5% acetic acid in water. The product was extracted with MTBE, and the organic layer concentrated to give crude product (7). This was treated with p-toluene sulfonic acid monohydrate (TsOH) in a tetrahydrofuran-methanol mixture. After completion of the reaction, the slurry was cooled and the product is isolated by filtration to give 12.2 kg of Compound 8.

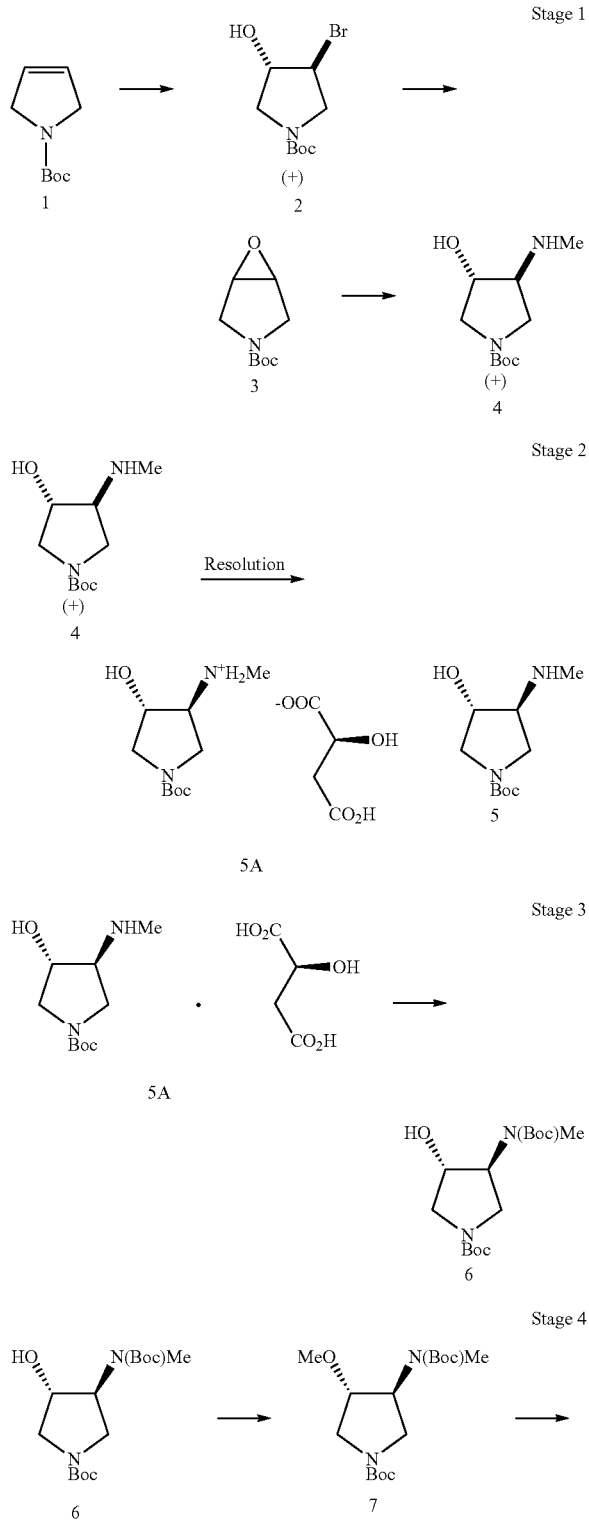

Synthesis of Compound 10

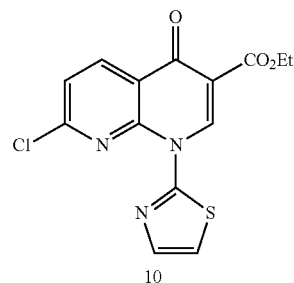

A solution of carbonyldiimidazole (CDI) (16.4 kg) in THF was added to a slurry of 2,6-dichloronicotinic acid (9) (16 kg) in THF. After about 2 hr, ethyl potassium malonate (EtO$_2$CCH$_2$CO$_2$K) (19.4 kg), triethylamine (25.9 kg) and magnesium chloride (11.9 kg) were added and the reaction stirred for about 24 hr. The reaction mixture was quenched with dilute HCl and extracted with ethyl acetate. The organic layer was concentrated, washed with a mixture of aqueous NaCl and NaHCO$_3$. The organic layer was diluted with methylcyclohexane and dried by vacuum distillation. The solution was treated with triethylorthoformate (17.1 kg) and acetic anhydride (59 kg) at about 90 to 110° C. After the reaction was judged to be complete, the excess acetic anhydride was removed by distillations with methylcyclohexane. The crude product was treated with a solution of 2-aminothiazole (8.2 kg) in THF. After about 2 hr, the reaction mixture was treated with potassium carbonate (13.6 kg) and the mixture stirred for about 6 hr. The product was precipitated by the addition of water, isolated by filtration, washed with ACN-water, ACN, and dried to give compound 10 (13.1 kg).

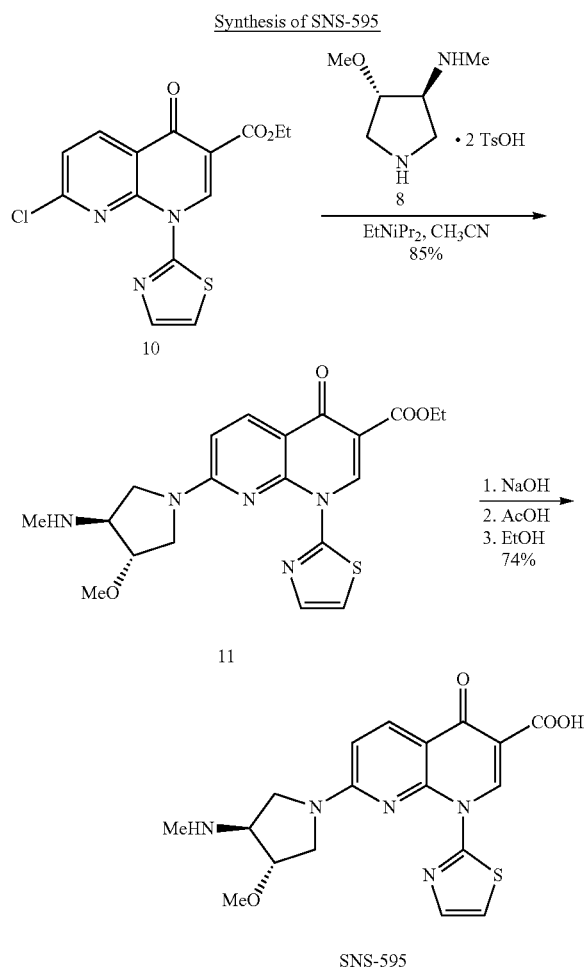

Synthesis of SNS-595

To a slurry of Compound 8 (8.0 kg) in ACN at about 5° C., N,N'-diisopropylethylamine (EtN$^i$Pr$_2$) (8.7 kg) was added. After about 15 min, Compound 10 (5.0 kg) was added to the reaction mixture. The reaction mixture was heated to about 45° C. for about 3 hr, cooled and the product filtered. The filter cake was washed with ACN and dried to give Compound 11 (5.5 kg).

To a solution of NaOH (0.8 kg) in water (19.5 kg), Compound 10 (5.5 kg) and ethanol (EtOH, 0.5 kg) were added. After hydrolysis was complete, the reaction mixture was filtered and the filtrate acidified to pH 7.3 to 7.7 by the addition of acetic acid. The mixture was then heated to about 55 to 65° C. for about 2 hr. After cooling to ambient temperature, the reaction mixture was filtered and washed with water and then with ethyl alcohol. The filter cake was dried under vacuum. The crude product was slurried in EtOH at about 80° C. After cooling, the product was filtered, washed with EtOH and dried to give SNS-595 (3.8 kg). Weight percent purity of SNS-595 was determined to be 99.9%.

Example 4

Pharmaceutical Composition Suitable for Injection or Intravenous Infusion

An illustrative example of a suitable pharmaceutical composition comprises: 10 mg of SNS-595 and (+)-1,4-dihydro-7-[(3S,4S)-3-methoxy-4-amino-1-pyrrolidinyl]-4-oxo-1-(2-thiazolyl)-1,8-naphthyridine-3-carboxylic acid (wherein the amount of SNS-595 is at least 99.95% and the amount of (+)-1,4-dihydro-7-[(3S,4S)-3-methoxy-4-amino-1-pyrrolidinyl]-4-oxo-1-(2-thiazolyl)-1,8-naphthyridine-3-carboxylic acid is less than about 0.05%) per milliliter (mL) of an aqueous 4.5% solution of sorbitol, that is adjusted to pH 2.5 with methanesulfonic acid. One protocol for making such a solution includes the following for making a 100 mg/10 mL presentation: 100 mg of an active composition, which consists essentially of at least 99.95% SNS-595 and less than 0.05% (+)-1,4-dihydro-7-[(3S,4S)-3-methoxy-4-amino-1-pyrrolidinyl]-4-oxo-1-(2-thiazolyl)-1,8-naphthyridine-3-carboxylic acid, and 450 mg D-sorbitol are added to distilled water; the volume is brought up to a volume of 10 mL; and the resulting solution is adjusted to pH 2.5 with methanesulfonic acid. The resulting composition is also suitable for lyophilization. The lyophilized form is then reconstituted with sterile water to the appropriate concentration prior to use.

Example 5

Pharmaceutical Composition Suitable for Injection or Intravenous Infusion

The embodiments of the claimed subject matter described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.
What is claimed is:
1. A compound selected from
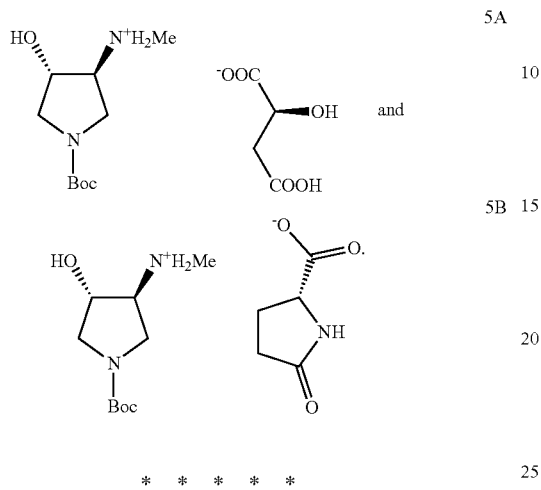

An illustrative example of a suitable pharmaceutical composition comprises: 10 mg of total of SNS-595 and impurities (wherein the amount of SNS-595 is at least about 99.95% and the total amount of impurity is less than about 0.05%) per mL of aqueous solution of 4.5% sorbitol that is adjusted to pH 2.5 with methanesulfonic acid. One protocol for making such a solution includes the following for making a 100 mg/10 mL presentation: 100 mg composition consisting essentially of at least about 99.95% SNS-595 and less than about 0.05% impurities and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.